US006153442A

United States Patent [19]
Pirio et al.

[11] Patent Number: 6,153,442
[45] Date of Patent: Nov. 28, 2000

[54] REAGENTS AND METHODS FOR SPECIFIC BINDING ASSAYS

[75] Inventors: Marcel Rene Pirio; Dariush Davalian, both of San Jose; Jacqueline Sadakan Ishkanian, San Mateo; Edwin F. Ullman, Atherton, all of Calif.

[73] Assignee: Dade Behring Inc., Deerfield, Ill.

[21] Appl. No.: 09/081,873

[22] Filed: May 20, 1998

[51] Int. Cl.⁷ ..................... G01N 33/545; G01N 33/532; C07D 495/04

[52] U.S. Cl. .............................. 436/533; 435/6; 435/7.5; 436/500; 436/531; 436/532; 436/534; 436/544; 436/815; 436/817; 548/303.7

[58] Field of Search ..................... 435/7.5, 6; 548/304.1, 548/303.7; 436/533, 500, 531, 532, 534, 544, 815, 817

[56] References Cited

U.S. PATENT DOCUMENTS

| | | |
|---|---|---|
| Re. 29,169 | 4/1977 | Schuurs et al. . |
| 3,817,837 | 6/1974 | Rubenstein et al. . |
| 3,996,345 | 12/1976 | Ullman et al. . |
| 4,098,876 | 7/1978 | Piasio et al. . |
| 4,233,402 | 11/1980 | Maggio et al. . |
| 4,244,940 | 1/1981 | Jeong et al. . |
| 4,264,766 | 4/1981 | Fischer ...................................... 536/46 |
| 4,275,149 | 6/1981 | Litman et al. ........................... 435/810 |
| 4,298,685 | 11/1981 | Parikh et al. ............................ 435/188 |
| 4,318,980 | 3/1982 | Boguslaski et al. ..................... 435/188 |
| 4,474,878 | 10/1984 | Halbert et al. ........................... 436/531 |
| 4,486,530 | 12/1984 | David et al. .............................. 436/519 |
| 4,535,057 | 8/1985 | Dreesman et al. ....................... 436/510 |
| 4,707,440 | 11/1987 | Stavrianopoulos ........................... 435/6 |
| 4,857,453 | 8/1989 | Ullman et al. ........................... 436/807 |
| 4,868,104 | 9/1989 | Kurn et al. ................................... 435/6 |
| 4,959,303 | 9/1990 | Milburn et al. .......................... 436/531 |
| 5,089,390 | 2/1992 | Davalian et al. ........................ 436/536 |
| 5,185,243 | 2/1993 | Ullman et al. ................................ 435/6 |
| 5,219,764 | 6/1993 | Huber et al. ............................. 436/536 |
| 5,340,716 | 8/1994 | Ullman et al. ................................ 435/6 |
| 5,514,559 | 5/1996 | Markert-Hahn et al. .............. 435/7.92 |

FOREIGN PATENT DOCUMENTS

WO 90/04791   5/1990   WIPO .

OTHER PUBLICATIONS

Wilbur, et al.; *Journal of Labelled Compounds and Radiopharmaceuticals*; Investigation of Biotin Dimers and Trimers for Increasing the Quantity of Radioactivity on Cancer Cells in Tumor Pretargeting. in vitro Demonstration of Streptavidin Cross–Linking; 40:335–337; 1997.

Luppa, et al.; *Bioconjugate Chem*; Synthesis of 3–Hydroxyestra–1,3,5(10)–trien–17–one and 33,17β–Dihydroxyestra–1,3,5(10–triene 6α–N–(ε–Biotinyl)caproamide, Tracer Substances for Developing Immunoassays for Estrone and Estradiol; 5/2:167–171; Mar. 1, 1994.

Mares, et al.; *Journal of Immunological Methods*; Synthesis of a Novel Biotin–Estradiol Conjugate and its Use for the Development of a Direct, Broad Range Enzyme Immunoassay for Plasma Estradiol; 183/2:211–219; Jun. 28, 1995.

Masanori, Oka; *Patent Abstracts of Japan*; Labeled Primer in Non–Ri Sequencing; vol. 018, No. 371; Jul, 13, 1994 (Abstract of Japanese Patent 061,005/86, Toyobo Co Ltd).

Morgan, et al; *Mol Cryst Liq Cryst*; Self–Assembly of Streptavidin/Bisbiotin Monolayers and Multilayers; 235:121–126; 1993.

Margel, S.; *Affinity Separation with Polyaldehyde Microsphere Beads*; J. Chromatography; 462:177–189; 1989.

Welsh, K. I.; *Antibody production made easier*; Nature; 266:495; Apr. 7, 1977.

Wade, N.; Hybridomas: *A Potent New Biotechnology*; Science; 208:692–693; 1980.

Galfrè, et al.; *Preparation of Monoclonal Antibodies: Strategies and Procedures*; Methods In Enzymology; 73 (Part B):3–46; 1981.

Green, N. Michael; *Avidin and Streptavidin*; Methods in Enzymology; 184 Chp. #5:51–67; 1990.

Akiyama et al; *Biotin Derivatives of Endothelin: Utilization for Affinity Purification of Endothelin Receptor*; Protein Expression and Purification; 3:427–433; 1992.

Basak et al; *Biotinylation of an Enkephalin–Containing Heptapeptide via Various Spacer Arms. Synthesis, Comparative Binding Studies toward Avidin and Application as Substrates in Enzymatic Reactions*; Bioconjugate Chem.; 5:301–305; 1994.

Morgan et al.; *Polymerization of Avidin and Streptavidin with Aromatic Bisbiotin Ligands*; J of Polymer Science, Part A Polymer Chem; 32:1331–1340; 1994.

Pierlot et al; *Solid Phase Synthesis of 5' Non Radioactive Multiple Labelled Oligodesoxyribonucleotides*; Journal of Med Chem Letters: 2:267–270; 1992.

Weber et al.; *Structural Origins of High–Affinity Biotin Binding to Streptavidin*; Science; 243:85–88; Jan. 6, 1989.

Nutikka et al; *Synthesis and Structural Characterization of a Cardioactive Biotinylated Digoxin Analogue*; Clin Biochem; 24:469–473; 1991.

Green et al.; *The Use of Bifunctional Biotinyl Compounds to Determine the Arrangement of Subunits in Avidin*; Biochem. J. (GB); 125:781–791; 1971.

(List continued on next page.)

*Primary Examiner*—Mary E. Ceperley
*Attorney, Agent, or Firm*—Patrick G. Gattari

[57] ABSTRACT

The present invention relates to compounds that are bis-biotins. These compounds comprise two biotinyl radicals connected by a chain of atoms, usually at least 16 atoms in length. The bis-biotin is conjugated to a member of a specific binding pair ("sbp member") wherein the chain is not part of the sbp member. Also disclosed are compositions comprising a complex of avidin and a bis-biotin as described above. The compounds and compositions of the invention find use in an assay for an analyte wherein there is employed a reagent system comprising an avidin reagent and a biotin reagent. The improvement of the present invention comprises using as the biotin reagent a bis-biotin as described above. Also disclosed are kits comprising the present bis-biotins and methods of preparing a bis-biotinylated conjugate of a member of a specific binding pair ("sbp member") for use in a specific binding assay.

43 Claims, 1 Drawing Sheet

OTHER PUBLICATIONS

Livnah et al; *Three–Dimensional Structures of Avidin and the Avidin–Biotin Complex*; Proc Natl Acad Sci.; 90:5076–5080; Jun. 1993.

Cuatrecases, P.; *Protein Purification by Affinity Chromatography*; J. Biol. Chem. 245:3059–3065, 1970.

Yallow, et al. *Immunoassay of Endogenous Plasma Insulin in Man*; J. Clin Invest; 39:1157–1175, 1960.

Kohler & Milstein; *Continuous cultures of fused cells secreting antibody of predefined specificity*; Nature; 256:495–497, 1975.

Wilbur et al; *Biotin Reagents for Antibody Pretargeting. 2. Synthesis and in Vitro Evaluation of Biotin Dimers and Trimers for Cross–Linking of Streptavidin*; Bioconjugate Chem.; 8:819–832; 1997.

Cook et al; *Synthesis and hybridization of a series of biotinylated oligonucleotides*; Nucleic Acids Research; 16 #9:4077–4095; 1988.

Green, N.M.; *Avidin*; Adv. Protein, Chem.; 29;85–133; 1975.

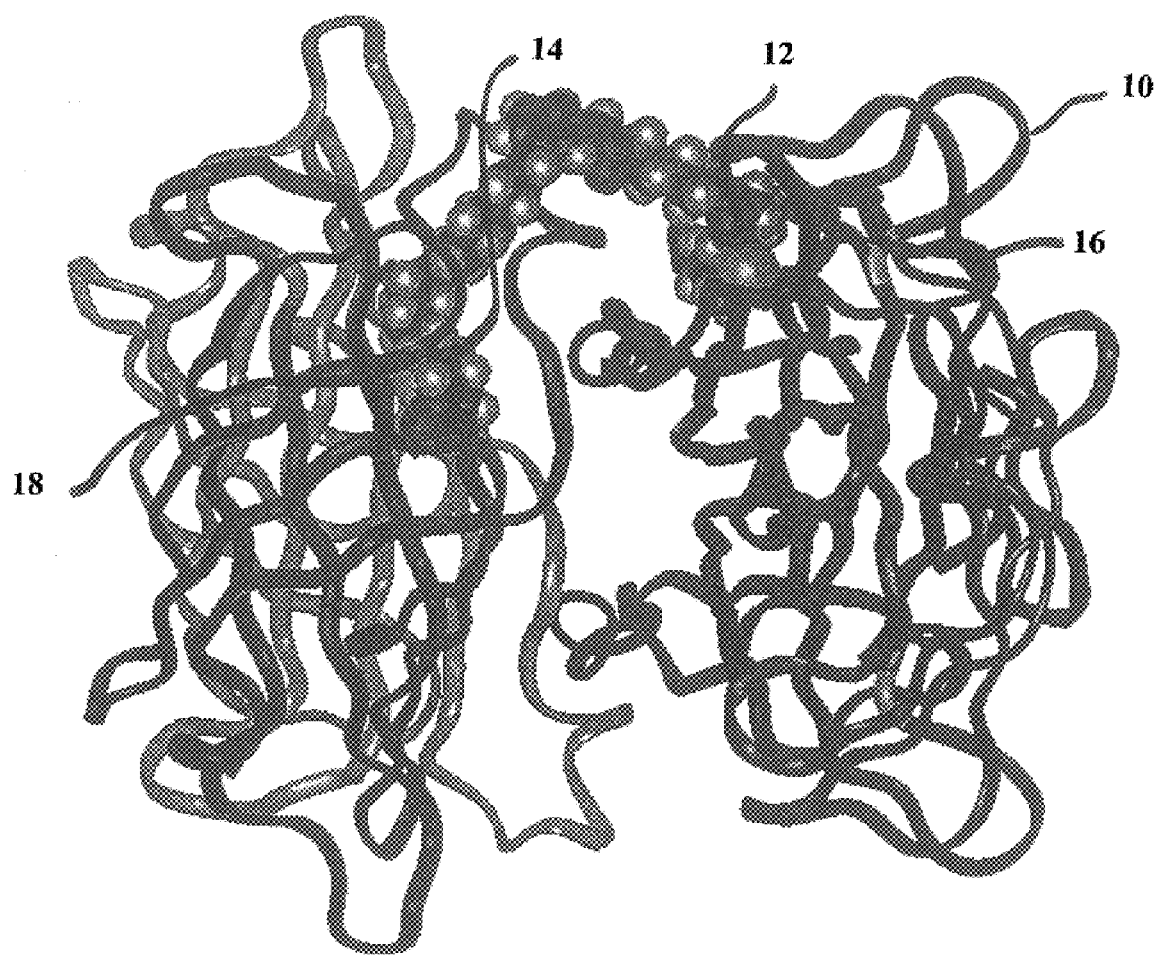

REAGENTS AND METHODS FOR SPECIFIC BINDING ASSAYS

BACKGROUND OF THE INVENTION

1. Field of the Invention

The present invention relates to bis-biotin compounds and compositions that find use, for example, in assays for analytes, such as, e.g., immunoassays, receptor assays and nucleic acid assays. In such assays it is often necessary to bind together two components, one being, for example, a specific binding member and the other being another assay component such as, for example, surfaces, antigens, haptens, nucleic acids, proteins such as antibodies, etc.

It has been found that reagents containing biotin are convenient for use in such assays. Such biotin reagents generally have one of the components to be bound conjugated to biotin. An avidin reagent is also employed that has avidin or streptavidin bound to the other of the components to be bound. To bring about binding of the two components, it is merely necessary to combine the biotin reagent with the avidin reagent. The binding interactions between biotin and the biotin binding site of avidin are the result of, among others, formation of multiple hydrogen bonds and van der Waals interactions between biotin and avidin together with the ordering of surface polypeptide loops that bury the biotin in the protein interior.

However, despite the strong binding of free biotin to avidin, biotin that is conjugated to another molecule does not bind as strongly. Assay components bound through biotin-avidin bonds can dissociate relatively rapidly during standing in dilute solutions or upon washing a surface to which they are attached. This phenomenon becomes particularly problematic in homogeneous assays where conjugates of specific binding pair members with labels may be stored in dilute solution for long periods prior to use.

Accordingly, there is a need for a binding pair that permits labeled assay components to bind to each other on mixing so efficiently that there is no free component that must be separated from the bound and there is no tendency of the bound component to dissociate even on standing for long periods of time.

Pairs of biotin molecules have previously been linked to each other through chains of varying lengths. There are reports of both monofunctional, namely, binding of one biotin, and bifunctional, namely, binding of both biotins, to avidin or streptavidin. Bis-biotins have been used to create ordered arrays of streptavidin through the formation of linear polymers of avidin or streptavidin. In situations where binding of bis-biotins has been bifunctional, indications are that only relatively weak binding was obtained. Multiple biotins have been attached to various sbp members. Usually, the preparations are random both with regard to the number and placement of the biotins, and most preparations utilize the sbp member as part of the chain linking the biotins. Generally, multiple biotins are attached because of the difficulty of attaching exactly one biotin or the opportunity to subsequently affix multiple labels through binding of multiple avidin molecules. Multiple biotins have been added to one terminus of an oligonucleotide because the biotins can be readily added by chain extension using terminal transferase. Also, avidin binds more efficiently at the oligonucleotide termini. In one case two biotins were deliberately introduced into an oligonucleotide at specific sites. The observed numbers of streptavidins that bound appeared to be additive and, thus, did not suggest bivalent binding.

2. Description of the Related Art

U.S. Pat. No. 4,298,685 (Parikh, et al.) discloses a diagnostic reagent for use in assays. The reagent is a conjugate of biotin and antibodies for the substance to be determined in the assay.

Hapten-biotin conjugates are discussed in U.S. Pat. No. 5,219,764 (Huber, et al.). In such conjugates the hapten is linked to biotin by means of a spacer, which has 26 to 40 atoms in its chain and contains at least 5 heteroatoms. The conjugates find use in certain homogeneous immunoassays.

Green discusses avidin and streptavidin complexes in *Methods in Enzymology* (1990) 184:51–67.

Green, et al., disclose the use of bifunctional biotinyl compounds to determine the arrangement of subunits in avidin (*Biochem. J.* (1971) 125:781–791).

Structural origins of high-affinity biotin binding to streptavidin is discussed by Weber, et al., in *Science* (1989) 243:85–88.

Morgan, et al., describe the polymerization of avidin and streptavidin with aromatic bis-biotin ligands in *Polym. Sci., Part A: Polym. Chem.* (1994) 32:1331.

Pierlot, et al., discloses solid phase synthesis of 5' non-radioactive multiple labeled oligodeoxyribonucleotides in *Bioorg. Med. Chem. Lett.* (1992) 2:267–271.

Akiyama discloses bis-biotinylated endothelin in *Protein Expression Purif.* (1992) 3:427.

The synthesis and structural characterization of a cardioactive biotinylated digoxin analogue is disclosed by Nutikka in *Clin. Bioch.* (1991) 24:469–473.

SUMMARY OF THE INVENTION

One aspect of the present invention is a compound that is a bis-biotin comprising two biotinyl radicals connected by a chain at least 16 atoms in length. The bis-biotin is conjugated to a member of a specific binding pair ("sbp member") where the chain is not part of the sbp member.

Another aspect of the present invention is a composition comprising a complex of avidin (as defined below) and a molecule having two biotinyl radicals connected to one another by a chain at least 16 atoms in length. The chain is conjugated to an sbp member where the chain is not part of the sbp member.

Another aspect of the present invention concerns an improvement in an assay for an analyte wherein there is employed a reagent system comprising an avidin reagent and a biotin reagent. The improvement comprises using as the biotin reagent a composition comprising two biotinyl radicals connected by a chain at least 16 atoms in length wherein an sbp member is conjugated to the chain and wherein none of the atoms of the chain is part of the sbp member.

Another aspect of the present invention is a kit comprising in packaged combination an avidin reagent and a compound consisting of a bis-biotin comprised of two biotinyl radicals connected by a chain at least 16 atoms in length. The bis-biotin is conjugated to an sbp member and the chain is not part of the sbp member.

Another aspect of the present invention is a method of preparing a bis-biotinylated conjugate of an sbp member for use in a specific binding assay. The method comprises the step of reacting the sbp member with a molecule containing two biotinyl radicals connected by a chain of at least 16 atoms. The chain comprises an attaching group for attaching the molecule to the sbp member.

Another embodiment of the present invention is a complex of (i) a compound that is a bis-biotin comprising two biotinyl radicals connected together and (ii) avidin. The bis-biotin is conjugated to a member of a specific binding pair ("sbp member") wherein the chain is not part of the sbp member. The complex remains substantially intact when stored for two weeks at 37° C. in a $10^{-6}$ M biotin solution.

Another embodiment of the present invention is a composition comprising avidin complexed with a bis-biotin having a chain, connecting two biotinyl radicals, of at least 16 atoms. The complexes have only one or two bis-biotin molecules bound to each avidin molecule.

Another aspect of the present invention is a compound comprising two biotinyl radicals covalently bound together by a linking group comprising a chain of atoms at least 16 atoms in length. The chain has an attaching group bound to it. The compound has the characteristic that, when a solution containing (i) less than or equal to $10^{-8}$ M of a 1:1 mole:mole complex of the compound and fully active avidin and (ii) $10^{-6}$ M free biotin is incubated at 37° C. for at least two weeks, the complex exhibits less than 1% dissociation.

Another aspect of the present invention is a compound that is a bis-biotin comprising two biotinyl radicals connected by a chain at least 16 atoms in length wherein the chain comprises a functionality reactive with a corresponding functionality of a protein. The functionality and the corresponding functionality are further characterized in that their reaction with each other does not substantially affect the ability of an sbp member to bind to the protein.

BRIEF DESCRIPTION OF THE DRAWINGS

FIG. 1 is a molecular depiction of a composition in accordance with the present invention.

DESCRIPTION OF THE SPECIFIC EMBODIMENTS

Bis-biotin compounds are provided wherein the two biotinyl radicals are joined by a chain of atoms such that increased stability of complexes with avidin (as defined below) is obtained by bivalent binding of the bis-biotin to the avidin. The chain of atoms has an attaching group that covalently bonds the bis-biotin to specific binding pair members such as haptens, proteins, receptors and nucleic acids or to a compound capable of generating electromagnetic radiation. The attaching group is located so that the specific binding pair member, when complexed to its complementary member does not interfere with binding of the biotinyl radicals to avidin and similarly binding of the biotinyl radicals to avidin does not interfere with binding of the sbp member to its complementary member. Furthermore, the attaching group is designed so as to cause minimal interference with the binding of either of the biotinyl radicals to the biotin binding sites of the same avidin molecule. The chain of atoms between the two biotins does not include any part of the sbp member and is designed to promote binding of both of the biotinyl radicals to the biotin binding sites of the same avidin molecule. In the bis-biotin compounds of the present invention the biotinyl radicals occupy the biotin binding sites of avidin in substantially the same manner as free biotin.

The present bis-biotin compounds are distinguished from known compositions wherein multiple biotins are bound to an sbp member by means of a bond or linking group. In these known compositions there is a distribution of compounds with varying number of biotins or each biotin molecule is bound to a separate functional group on the sbp member. Accordingly, at least some part of the chain of atoms linking the two biotins in the known compounds comprises the sbp member. Thus, simultaneous binding of the sbp member to its complementary member and efficient binding of both biotins to the same avidin molecule is inhibited. In the present bis-biotin compounds the linking chain between the two biotins does not comprise any part of an sbp member that is attached to the linking chain by means of a bond or an attaching group.

Before proceeding further with a description of the specific embodiments of the present invention, a number of terms will be defined and described in detail.

Avidin—the term "avidin" is used herein generically and includes any biotin-binding protein other than an immunoglobulin that binds biotin including both natural proteins and recombinant and genetically engineered proteins. The term includes the two common biotin-binding proteins known as "egg white or avian avidin" and "streptavidin." Egg white or avian avidin, commonly referred to simply as avidin, is a protein that is a constituent of egg white and forms a noncovalent complex with biotin. Streptavidin is a protein isolated from the actinobacterium *Streptomyces avidinii* and also forms a noncovalent complex with biotin. Other bacterial sources of biotin binding proteins are also known. Both egg white avidin and streptavidin are tetrameric proteins in which the biotin binding sites are arranged in pairs on opposite faces of the avidin molecule. Accordingly, both of the above avidins have the ability to bind up to four molecules of biotin, either in the free form or in a derivative form and, thereby form a "complex." A derivative form of biotin results from the conjugation of biotin to another molecule. Because of the ability of avidin to bind a biotin derivative, avidin-biotin binding has been used in diagnostic assays, for example, to form reagent complexes either prior to or during an assay.

Bis-biotin—a compound comprising only two biotinyl radicals. The bis-biotin compounds of the present invention generally have the formula:

$$\begin{array}{c} B \\ D\,A\,W \\ B \end{array}$$

wherein B is a biotinyl radical, D is a chain, connecting the biotinyl radicals, usually of at least 16 atoms, A is a bond or an attaching group and W is a member of a specific binding pair or a group detectable by means of electromagnetic radiation or by electrochemical detection.

Some of the bis-biotin compounds of the invention are represented by the formula:

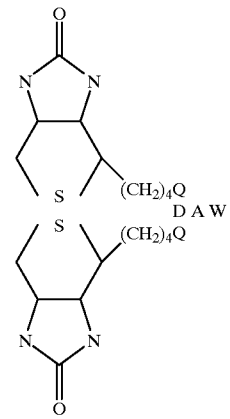

wherein Q is independently selected from the groups consisting of:

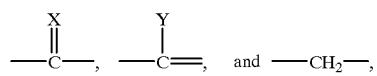

and wherein X is selected from a group consisting of O, S, NH, and NR; and Y is selected from the group consisting of H, OR, SR, NHR and $NR_2$ wherein R is lower alkyl; and wherein D, A and W are as defined above.

Preferably, the bis-biotin compounds of the present invention have the above formula wherein Q is —C═X and wherein X, R, D, A and W are as defined above.

Biotinyl radical—a biotin moiety in the compounds of the present invention. The biotinyl radical has the formula:

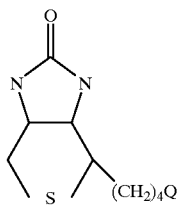

Chain of atoms—a chain usually of at least 16 atoms, preferably, 16–30 atoms, more preferably, 17–21 atoms, connecting two biotinyl radicals wherein only the smallest number of atoms connected to one another to form a chain are counted for the purpose of establishing the length of the chain in number of atoms. Other atoms may be connected to one or more atoms of the chain, but these atoms are not counted for the purpose of establishing the length of the chain. The nature of the chain including the number of atoms is best determined as described hereinbelow.

The atoms connected to one another to form the chain generally comprise carbon and may include one or more heteroatoms that usually occur in organic molecules. The usual heteroatoms are selected from the group consisting of nitrogen, oxygen, sulfur, boron, silicon and phosphorus. Preferably, heteroatoms in the chain are oxygen and/or nitrogen. The number of heteroatoms can vary depending on the number of functionalities in the chain. Usually, the number of heteroatoms forming the chain is from 0 to 10, preferably, 1 to 8, more preferably, 2 to 6.

As a matter of practicality, the number of atoms in the chain should not be so great that polymers are readily formed upon mixing the bis-biotin compound of the present invention with avidin. The longer the chain, the greater the ability of a compound having two biotins to cause polymerization by binding two molecules of avidin.

Of the atoms directly attached to the chains of the present invention, oxygen is normally present as oxo or oxy bonded to carbon, sulfur, silicon, nitrogen or phosphorous; nitrogen is normally present as azo, nitro, nitroso or amino, normally bonded to carbon, boron, nitrogen, or phosphorous; sulfur normally occurs as described above for oxygen; phosphorous is normally bonded to carbon or nitrogen, usually as phosphonate, phosphine or phosphine oxide. One or more of the atoms connected to one another to form a chain may form part of one or more rings wherein the other atoms of the ring are carbon, oxygen, sulfur, boron, silicon and/or nitrogen. Usually, the ring is a three to eight member ring, preferably, a five to seven member ring, that can have one or more unsaturations. The ring may be aryl or aralkyl and may be further substituted as described in more detail herein. One or more atoms of the chain may be substituted with a substituent other than hydrogen to form one or more functionalities.

Examples, by way of illustration and not limitation, of functionalities that may be present in, or attached to, the chain formed by the aforementioned atoms are: carboxylic acids, carboxylic acid esters, sulfonic acids, sulfonic acid esters, phosphoric acids, phosphoric acid esters, phosphonic acids, phosphonic acid esters, ureas, carbamates, carboxamides, phosphoramides, sulfonamides, ethers, sulfides, thioethers, olefins, acetylenes, amines, ketones, aldehydes and nitriles, and alkyl, cycloalkyl, alkylidine, aryl, aralkyl wherein the alkyl, cycloalkyl, alkylidine, aryl, and aralkyl may be substituted with a substituent other than hydrogen such as, e.g., alkoxy, aryloxy, aralkoxy and the like.

Preferably, the chain of atoms linking the two biotins in the present compounds has limited degrees of freedom of rotation. This is achieved by incorporating into the chain a group that does not permit free rotation such as, for example, a double or triple bond; one or more rings, and the like. In a preferred approach, the chain of atoms comprises at least 5 atoms in a rigid spatial array. Alternatively, the chain of atoms comprises at least two sets of at least 4 atoms in a rigid spatial array. By the term "rigid spatial array" is meant that one to three spacial relationships or conformations of the atoms in the array are energetically preferred, usually by at least 4 Kcal/mole, preferably by at least 6 Kcal/mole, over other possible conformations. Energetically preferred conformations may be achieved by having some or all of the atoms as part of a ring, either unsaturated or saturated. Chains comprising olefins, acetylenes, carboxamides, oximes, hydrazones, azo compounds, nitrones and the like all comprise rigid spacial arrays. Particularly preferred is inclusion of three atoms of an aromatic ring in the chain such as, for example, benzene, naphthalene, anthracene, phenanthrene, pyridine, pyrimidine furan, indene, indane, pyrrole, thiophene, imidazole, and the like. Preferably, the remaining atoms of the chain are symmetrical about the rigid spatial array, but need not be.

The following are typical examples, by way of illustration and not limitation, of a chain at least 16 atoms in length that may be employed in the present invention:

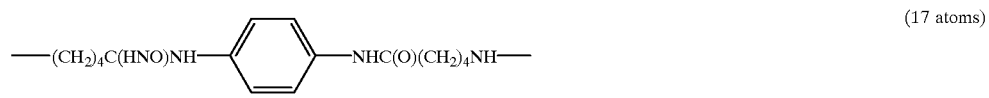

(17 atoms)

(16 atoms)

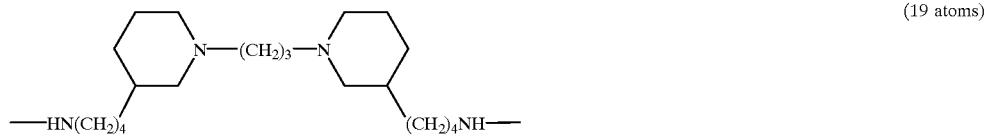

(19 atoms)

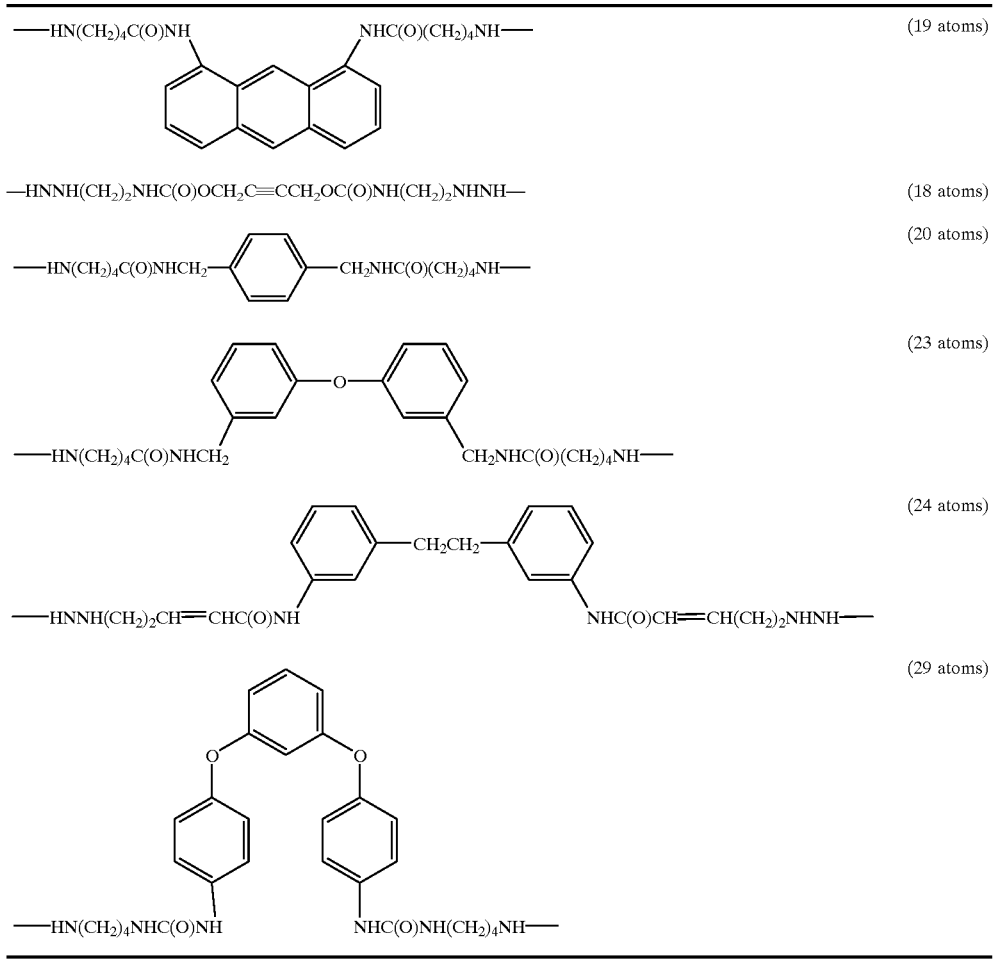

Attaching group—the group that covalently connects two substructures such as an sbp member or a group detectable electrochemically or by electromagnetic radiation, on the one hand, and the chain of atoms connecting two biotinyl radicals, on the other hand. The attaching group may vary from a bond to a chain of from 1 to 50 atoms, usually from about 1 to 40 atoms, preferably 1 to 10 atoms, each independently selected from the group normally consisting of carbon, oxygen, sulfur, nitrogen, and phosphorous. The number of heteroatoms in the attaching group normally ranges from about 0 to 20, usually from about 1 to 15, more preferably 2 to 6. The number of atoms in the chain is determined by counting the number of atoms other than hydrogen or other monovalent atoms along the shortest route between the substructures being connected. The atoms of the attaching group may be substituted with atoms other than hydrogen as described below. As a general rule, the length of a particular attaching group can be selected arbitrarily to provide for convenience of synthesis with the proviso that there be minimal interference caused by the attaching group with the ability of the two biotins to bind to avidin and with the binding of an sbp member to its complementary member.

The attaching group may be aliphatic or aromatic. When heteroatoms are present, oxygen will normally be present as oxo or oxy, bonded to carbon, sulfur, nitrogen or phosphorous, nitrogen will normally be present as nitro, nitroso or amino, normally bonded to carbon, oxygen, sulfur or phosphorous; sulfur would be analogous to oxygen; while phosphorous will be bonded to carbon, sulfur, oxygen or nitrogen, usually as phosphonate and phosphate mono- or diester. Functionalities present in the attaching group may include esters, thioesters, amides, thioamides, ethers, ureas, thioureas, guanidines, azo groups, thioethers, carboxylate and so forth.

The attaching group may be a single heteroatom such as oxygen or sulfur or NH or may comprise two linking members that provide for attachment of the attaching group to the chain and to the sbp member, respectively.

Functional groups that are normally present or are introduced into either the attaching group or an sbp member, on the one hand, and either the attaching group or the chain of atoms, on the other hand, are employed in forming the linking members for linking the sbp member and the chain, respectively, to the attaching group.

Preparation of the sbp member bound through an attaching group to a chain linking two biotinyl radicals can be carried out in any convenient manner. Normally, it will be convenient to synthesize a chain linking two biotinyl radicals that has a functional group within or attached to the chain that is suitable for covalent attachment to an sbp member or functionalized derivative of an sbp member. The functional groups of the chain and the sbp member may comprise some or all of the attaching group. As a matter of practicality, it is often desirable to have functional groups on the chain of atoms linking the biotinyl radicals and the sbp member that can be used to form covalent bonds under mild conditions. Useful pairs of groups that can react under mild conditions include, by way of example and not limitation, amine-carboxylic acid, amine-sulfonic acid, amine-iminoether, sulfhydryl-sulfhydryl, sulfhydryl-α-haloamide, sulfhydryl-maleimide, alcohol-phosphonic acid and the like. The members of these pairs can be covalently linked together by standard protocols. Preferably, the attaching group is constructed by direct coupling of the sbp member and the chain of atoms linking the biotinyl radicals or by coupling of each of these members to opposite ends of a chain of atoms that is to comprise the attaching group.

For the most part, there is employed a non-oxocarbonyl group including nitrogen and sulfur analogs, a phosphate group, an amino group, alkylating agent such as halo or tosylalkyl, oxy (hydroxyl or the sulfur analog, mercapto) oxocarbonyl (e.g., aldehyde or ketone), or active olefin such as a vinyl sulfone or a,b-unsaturated ester. Such functionality is then linked to amine groups, carboxyl groups, active olefins, alkylating agents, e.g., bromoacetyl, to form a linking member portion of the attaching group. Where an amine and carboxylic acid or its nitrogen derivative or phosphoric acid are linked, amides, amidines and phosphoramides will be formed. Where mercaptan and activated olefin are linked, thioethers will be formed. Where a mercaptan and an alkylating agent are linked, thioethers will be formed. Where aldehyde and an amine are linked under reducing conditions, an alkylamine will be formed. Where a carboxylic acid or phosphonic acid and an alcohol are linked, esters will be formed. For the most part, carbonyl functionalities find use in forming the linking members, both oxocarbonyl, e.g., carboxy and aldehyde, and non-oxocarbonyl (including nitrogen and sulfur analogs) e.g., amidine, imidate, isothiocyanate and thioesters. Alternative functionalities that find use in forming the linking members include active halogen, diazo, mercapto, olefin, particularly activated olefin, amino, alkylamine, sulfonate, and phosphate esters and the like. For sbp members that are proteins, the chain can comprise a functionality reactive with a corresponding functionality of a protein. The two functionalities are further characterized in that their reaction with each other does not substantially affect the ability of an sbp member to bind to the protein. Accordingly, it is desirable that at least 40%, preferably, at least 60%, and more preferably, at least 70% of the activity of the particular protein be retained. For example, the functionality that comprises part of the chain can be a functionality subject to nucleophilic substitution such as, e.g., non-oxocarbonyl, and the corresponding functionality of the protein can be a nucleophilic functionality such as, e.g., amino or sulfhydryl. Other such pairs of interactive functionalities are known in the art.

Examples, by way of illustration and not limitation, of various attaching groups that find use in the present invention are found in U.S. Pat. No. 3,817,837, particularly at column 30, line 69, to column 36, line 10, which disclosure is incorporated herein by reference in its entirety.

Alkyl—a monovalent branched or unbranched radical derived from an aliphatic hydrocarbon by removal of one H atom; includes both lower alkyl and upper alkyl.

Lower alkyl—alkyl containing from 1 to 5 carbon atoms such as, e.g., methyl, ethyl, propyl, butyl, isopropyl, isobutyl, pentyl, isopentyl, etc.

Upper alkyl—alkyl containing more than 6 carbon atoms, usually 6 to 20 carbon atoms, such as, e.g., hexyl, heptyl, octyl, etc.

Alkylidene—a divalent organic radical derived from an aliphatic hydrocarbon, such as, for example, ethylidene, in which 2 hydrogen atoms are taken from the same carbon atom.

Aryl—an organic radical derived from an aromatic hydrocarbon by the removal of one atom and containing one or more aromatic rings, usually one to four aromatic rings, such as, e.g., phenyl (from benzene), naphthyl (from naphthalene), etc., e.g., phenyl, naphthyl, phenanthryl.

Aralkyl—an organic radical having an alkyl group to which is attached an aryl group, e.g., benzyl, phenethyl, 3-phenylpropyl, 1-naphthylethyl, etc.

Alkoxy—an alkyl radical attached to the remainder of a molecule by an oxygen atom, e.g., methoxy, ethoxy, etc.

Aryloxy—an aryl radical attached to the remainder of a molecule by an oxygen atom, e.g., phenoxy, naphthoxy, etc., e.g., m-methoxyphenyl.

Aralkoxy—an aralkyl radical attached to the remainder of a molecule by an oxygen atom, e.g., benzoxy, 1-naphthylethoxy, etc.

Linking member—a portion of a structure which connects 2 or more substructures.

Conjugate—a molecule comprised of two or more substructures bound together, generally through a linking member, to form a single structure. The binding is by means of an attaching group. For example, an sbp member attached to a chain of atoms that connects two biotinyl radicals is a bis-biotin-sbp member conjugate or a compound capable of generating electromagnetic radiation attached to a chain of atoms that connects two biotinyl radicals is a bis-biotin-compound conjugate. In addition, biotinyl radicals connected by a chain of atoms is a bis-biotin conjugate.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormones-hormone receptors, nucleic acid duplexes, IgG-protein A, polynucleotide pairs such as DNA-DNA, DNA-RNA, and the like are not immunological pairs but are included in the definition of sbp member for the purpose of describing this invention.

Analyte—the compound or composition to be detected. The analyte can be comprised of a member of a specific binding pair (sbp) and may be a ligand, which is usually monovalent (monoepitopic), usually haptenic, and is a single compound or plurality of compounds which share at least one common epitopic or determinant site.

The monoepitopic ligand analytes will generally be from about 100 to 2,000 molecular weight, more usually from 125 to 1,000 molecular weight. The analytes include drugs, metabolites, pesticides, pollutants, and the like. Representative analytes, by way of example and not limitation, include (i) alkaloids such as morphine alkaloids, which includes morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites; (ii) steroids, which include the estrogens, androgens, andreocortical steroids, bile acids, cardiotonic glycosides and aglycones, which includes digoxin and digoxigenin, saponins and sapogenins, their derivatives and metabolites; steroid mimetic substances, such as diethylstilbestrol; (iii) lactams having from 5 to 6 annular members, which include the barbiturates, e.g. Phenobarbital and secobarbital, diphenylhydantoin, primidone, ethosuximide, and their metabolites; (iv) aminoalkylbenzenes, with alkyl of from 2 to 3 carbon atoms, which include the amphetamines; catecholamines, which includes ephedrine, L-dopa, epinephrine; narceine; papaverine; and metabolites of the above; (v) benzheterocyclics which include oxazepam, chlorpromazine, tegretol, their derivatives and metabolites, the heterocyclic rings being azepines, diazepines and phenothiazines; (vi) purines, which includes theophylline, caffeine, their metabolites and derivatives; (vii) drugs derived from marijuana, which includes cannabinol and tetrahydrocannabinol; (viii) hormones such as thyroxine, cortisol, triiodothyronine, testosterone, estradiol, estrone, progesterone, polypeptides such as angiotensin, LHRH, and immunosuppressants such as cyclosporin, FK506, mycophenolic acid (MPA), and so forth; (ix) vitamins such as A, B, e.g. B12, C, D, E and K, folic acid, thiamine; (x) prostaglandins, which differ by the degree and sites of hydroxylation and unsaturation; (xi) tricyclic antidepressants, which include imipramine, dismethylimipramine, amitriptyline, nortriptyline, protriptyline, trimipramine, chlomipramine, doxepine, and desmethyldoxepin; (xii) anti-neoplastics, which include methotrexate; (xiii) antibiotics, which include penicillin, chloromycetin, actinomycetin, tetracycline, terramycin, the metabolites and derivatives; (xiv) nucleosides and nucleotides, which include ATP, NAD, FMN, adenosine, guanosine, thymidine, and cytidine with their appropriate sugar and phosphate substituents; (xv) miscellaneous individual drugs which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, their metabolites and derivatives; (xvi) metabolites related to diseased states include spermine, galactose, phenylpyruvic acid, and porphyrin Type 1; (xvii) aminoglycosides, such as gentamicin, kanamicin, tobramycin, and amikacin; and (xviii) pesticides such as polyhalogenated biphenyls, phosphate esters, thiophosphates, carbamates, polyhalogenated sulfenamides, their metabolites and derivatives.

Polyvalent analytes are normally poly(amino acids), i.e., polypeptides and proteins, polysaccharides, nucleic acids, and combinations thereof. Such combinations include components of bacteria, viruses, chromosomes, genes, mitochondria, nuclei, cell membranes and the like. For the most part, the polyepitopic ligand analytes will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc. Such proteins include, for example, immunoglobulins, cytokines, enzymes, hormones, cancer antigens, nutritional markers, tissue specific antigens, etc. Such proteins include, by way of illustration and not limitation, protamines, histones, albumins, globulins, scleroproteins, phosphoproteins, mucoproteins, chromoproteins, lipoproteins, nucleoproteins, glycoproteins, T-cell receptors, proteoglycans, HLA, unclassified proteins, e.g., somatotropin, prolactin, insulin, pepsin, proteins found in human plasma, blood clotting factors, protein hormones such as, e.g., follicle-stimulating hormone, luteinizing hormone, luteotropin, prolactin, chorionic gonadotropin, tissue hormones, cytokines, cancer antigens such as, e.g., PSA, CEA, a-fetoprotein, acid phosphatase, CA19.9 and CA125, tissue specific antigens, such as, e.g., alkaline phosphatase, myoglobin, CPK-MB and calcitonin, and peptide hormones. Other polymeric materials of interest are mucopolysaccharides and polysaccharides.

For receptor analytes, the molecular weights will generally range from 10,000 to $2 \times 10^8$, more usually from 10,000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

The term analyte further includes oligonucleotide and polynucleotide analytes such as m-RNA, r-RNA, t-RNA, DNA, DNA-RNA duplexes, etc.

The analyte may be a molecule found directly in a sample such as biological tissue, including body fluids, from a host. The sample can be examined directly or may be pretreated to render the analyte more readily detectable by removing unwanted materials. The sample may be pretreated to separate or lyse cells; precipitate, hydrolyse or denature proteins; hydrolyze lipids; solubilize the analyte; or the like. Such pretreatment may include, without limitation: centrifugation; treatment of the sample with an organic solvent, for example, an alcohol, such as methanol; and treatment with detergents. The sample can be prepared in any convenient medium which does not interfere with an assay. An aqueous medium is preferred.

The analyte of interest may be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay.

The biological tissue includes excised tissue from an organ or other body part of a host and body fluids, for example, urine, whole blood, plasma, serum, saliva, semen, stool, sputum, cerebral spinal fluid, tears, mucus, and the like. Preferably, the sample is plasma or serum.

Polynucleotide—a compound or composition which is a polymeric nucleotide having in the natural state about 50 to 500,000 or more nucleotides and having in the isolated state about 15 to 50,000 or more nucleotides, usually about 15 to 20,000 nucleotides, more frequently 15 to 10,000 nucleotides. Polynucleotide includes nucleic acids from any source in purified or unpurified form, naturally occurring or synthetically produced, including DNA (dsDNA and ssDNA) and RNA, usually DNA, and may be t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like.

Ligand—any organic compound for which a receptor naturally exists or can be prepared.

Hapten—a compound capable of binding specifically to corresponding antibodies, but does not itself act as an immunogen (or antigen) for preparation of the antibodies. Antibodies which recognize a hapten can be prepared against compounds comprised of the hapten linked to an immunogenic (or antigenic) carrier. Haptens are a subset of ligands.

Ligand analog—a modified ligand, an organic radical or analyte analog, usually of a molecular weight greater than 100, which can compete with the analogous ligand for a receptor, the modification providing means to join a ligand analog to another molecule. The ligand analog will usually differ from the ligand by more than replacement of a hydrogen with a bond which links the ligand analog to a hub or label, but need not. The ligand analog can bind to the receptor in a manner similar to the ligand. The analog could be, for example, an antibody directed against the idiotype of an antibody to the ligand.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component C1q, and the like.

Specific binding—the specific recognition of one of two different molecules for the other compared to substantially less recognition of other molecules. Generally, the molecules have areas on their surfaces or in cavities, also referred to as "binding sites," giving rise to specific recognition between the two molecules. Exemplary of specific binding are antibody-antigen interactions, enzyme - substrate interactions, polynucleotide interactions, and so forth.

Non-specific binding—non-covalent binding between molecules that is relatively independent of specific surface structures. Non-specific binding may result from several factors including hydrophobic interactions between molecules.

Antibody—an immunoglobulin which specifically binds to and is thereby defined as complementary with a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and $F(ab')_2$, Fab', and the like. In addition, aggregates, polymers, and conjugates of immunoglobulins or their fragments can be used where appropriate so long as binding affinity for a particular molecule is maintained.

Substituted—means that a hydrogen atom of a molecule has been replaced by another atom, which may be a single atom such as a halogen, etc., or part of a group of atoms forming a functionality as described above. Such substituent may be a group or functionality imparting hydrophilicity or lipophilicity. Hydrophilicity may be achieved by a functional group having a sulfonate, sulfate, phosphate, amidine, phosphonate, carboxylate, hydroxyl particularly polyols, amine, ether, amide, and the like. Illustrative functional groups are carboxyalkyl, sulfonoxyalkyl, $CONHOCH_2COOH$, CO-(glucosamine), sugars, dextran, cyclodextrin, $SO_2NHCH_2COOH$, $SO_3H$, $CONHCH_2CH_2SO_3H$, $PO_3H_2$, $OPO_3H_2$, hydroxyl, carboxyl, ketone, and combinations thereof. Lipophilicity may be achieved by a functional group such as carbon atoms substituted with hydrogen or halogen and can include alkyl, alkylidene, aryl and aralkyl. The lipophilic group or functionality will normally have one to six straight or branched chain aliphatic groups of at least 6 carbon atoms, more usually at least 10 carbon atoms, and preferably at least 12 carbon atoms, usually not more than 30 carbon atoms.

Support or surface—a solid phase, typically a support or surface, which is a porous or non-porous water insoluble material that can have any one of a number of shapes, such as strip, rod, plate, well, particle or bead. A wide variety of suitable supports are disclosed in Ullman, et al. U.S. Pat. No. 5,185,243, columns 10–11, Kurn, et al., U.S. Pat. No. 4,868,104, column 6, lines 21–42 and Milburn, et al., U.S. Pat. No. 4,959,303, column 6, lines 14–31, which are incorporated herein by reference.

The surface can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly (vinyl butyrate), etc.; either used by themselves or in conjunction with other materials; glass available as Bioglass, ceramics, metals, and the like. Natural or synthetic assemblies such as liposomes, phospholipid vesicles, and cells can also be employed.

Binding of sbp members to a support or surface, other than by use of the compounds of the present invention, may be accomplished by well-known techniques, commonly available in the literature. See, for example, "Immobilized Enzymes," Ichiro Chibata, Halsted Press, New York (1978) and Cuatrecasas, *J. Biol. Chem.,* 245:3059 (1970).

Signal producing system ("sps")—one or more components, at least one component being a detectable label, which generate a detectable signal that relates to the amount of bound and/or unbound label, i.e. the amount of label bound or not bound to the compound being detected. The label is any molecule that produces or can be induced to produce a signal, and may be, for example, a fluorescer, radio-label, enzyme, chemiluminescer or photosensitizer. Thus, the signal is detected and/or measured by detecting enzyme activity, luminescence, light absorbance or radioactivity as the case may be.

Suitable labels include, by way of illustration and not limitation, enzymes such as alkaline phosphatase, glucose-6-phosphate dehydrogenase ("G6PDH") and horseradish peroxidase; ribozyme; a substrate for a replicase such as QB replicase; promoters; dyes; fluorescers, such as fluorescein, isothiocyanate, rhodamine compounds, phycoerythrin, phycocyanin, allophycocyanin, o-phthaldehyde, and fluorescamine; chemiluminescers such as isoluminol; sensitizers; coenzymes; enzyme substrates; radiolabels such as $^{125}I$, $^{131}I$, $^{14}C$, $^{3}H$, $^{57}Co$ and $^{75}Se$; particles such as latex or carbon particles; metal sol; crystallite; liposomes; cells, etc., which may be further labeled with a dye, catalyst or other detectable group. Suitable enzymes and coenzymes are disclosed in Litman, et al., U.S. Pat. No. 4,275,149, columns 19–28, and Boguslaski, et al., U.S. Pat. No. 4,318,980, columns 10–14; suitable fluorescers and chemiluminescers are disclosed in Litman, et al., U.S. Pat. No. 4,275,149, at columns 30 and 31; which are incorporated herein by reference.

There are numerous methods by which the label can produce a signal detectable by external means, desirably by visual examination, for example, by electromagnetic radiation, heat, and chemical reagents. The label or other sps members can also be bound to an sbp member, another molecule or to a support.

Labels include groups detectable by means of electromagnetic radiation or by electrochemical detection including dyes, fluorescers, chemiluminescers, and radioactive isotopes.

The label can directly produce a signal, and therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes.

Alternately, the label may need other components to produce a signal, and the signal producing system would then include all the components required to produce a measurable signal, which may include substrates, coenzymes, enhancers, additional enzymes, substances that react with enzymic products, catalysts, activators, cofactors, inhibitors, scavengers, metal ions, and a specific binding substance required for binding of signal generating substances. A detailed discussion of suitable signal producing systems can be found in Ullman, et al. U.S. Pat. No. 5,185,243, columns 11–13, incorporated herein by reference.

The label and/or other sps member may be bound to an sbp member or to a support utilizing the compounds and compositions of the present invention. Alternatively, the label can be bound covalently to an sbp member such as, for example, an antibody; a receptor for an antibody, a receptor that is capable of binding to a small molecule conjugated to an antibody, or a ligand analog. Bonding of the label to the sbp member may be accomplished by chemical reactions that result in replacing a hydrogen atom of the label with a bond to the sbp member or may include a linking group between the label and the sbp member. Other sps members may also be bound covalently to sbp members. For example, two sps members such as a fluorescer and quencher can each be bound to a different antibody that forms a specific complex with the analyte. Formation of the complex brings the fluorescer and quencher in close proximity, thus permitting the quencher to interact with the fluorescer to produce a signal. Methods of conjugation are well known in the art. See for example, Rubenstein, et al., U.S. Pat. No. 3,817,837, incorporated herein by reference.

Assay—method for the determination of the presence or amount of an analyte.

Measuring the amount of an analyte—quantitative, semiquantitative, and qualitative methods as well as all other methods for determining an analyte are considered to be methods of measuring the amount of an analyte. For example, a method which merely detects the presence or absence of an analyte in a sample suspected of containing the analyte is considered to be included within the scope of the present invention. The terms "detecting" and "determining", as well as other common synonyms for measuring, are contemplated within the scope of the present invention.

Ancillary Materials—Various ancillary materials will frequently be employed in the assay in accordance with the present invention. For example, buffers will normally be present in the assay medium, as well as stabilizers for the assay medium and the assay components. Frequently, in addition to these additives, proteins may be included, such as albumins; organic solvents such as formamide; quaternary ammonium salts; polyanions such as dextran sulfate; surfactants, particularly non-ionic surfactants; binding enhancers, e.g., polyalkylene glycols; or the like.

Wholly or partially sequentially—when the sample and various agents utilized in the present invention are combined other than concomitantly (simultaneously), one or more may be combined with one or more of the remaining agents to form a subcombination. Each subcombination can then be subjected to one or more steps of the present method. Thus, each of the subcombinations can be incubated under conditions to achieve one or more of the desired results.

As mentioned above, one aspect of the present invention is a compound that is a bis-biotin comprising two biotinyl radicals connected by a chain of atoms. The bis-biotin is conjugated to an sbp member wherein no part of the chain is part of the sbp member. In the present bis-biotin compounds the sbp member is attached to the chain of atoms by means of an attaching group. The biotinyl radicals of the present compounds can occupy adjacent biotin binding sites on a single molecule of avidin in substantially the same manner as free biotin molecules.

The compounds of the invention can be prepared by a combination of procedures that are known in the art. The carboxylic acid functionality on the biotin can be used for the attachment of the biotinyl radical to a group that will ultimately form all or part of the chain connecting the two biotinyl radicals. The carboxylic acid can be reduced to an aldehyde or alcohol or directly activated for reaction with a corresponding molecule. Many methods for activation of the carboxylic acid group are known such as, for example, conversion to an active ester such as a N-hydroxysuccinimide ester, p-nitrophenyl ester, phenyl thioester, and the like; a mixed anhydride such as, for example, by reaction with a chlorocarbonate mixed anhydride; a carboxylic acid halide; activation by a carbodiimide; and so forth. The biotin having an activated carboxylic acid group is reacted preferably with a bifunctionalized reagent that includes a chain of at least 16 atoms for connecting the biotinyl radicals. Thus, the activated carboxylic acid group of the biotin can react with available nucleophilic groups such as amines, active methylene groups, alcohols, enamines, etc., on the bifunctionalized reagent. Alternatively, the biotin carboxylic acid can be reduced to an aldehyde and reacted with amines by reductive amination, or with hydrazines, hydroxylamines, hydrazides and the like present in the bifunctionalized reagent. The alcohol produced by reduction of the carboxylic acid of biotin can likewise be reacted with the bifunctionalized reagent by reaction with active esters, alkylating groups such as α-bromoamides and the like or the alcohol can be converted to a leaving group such as tosylate or bromide reacted with groups on the bifunctionalized reagent such as alcohols, amines, thiols, and the like. The reagent is bifunctionalized in that it has two functionalities for linking to the two activated biotinyl radicals. This reagent is comprised of a chain of atoms terminated at each end in a functional group designed to react with the activated biotinyl radical to produce a chain usually of at least 16 atoms and also contains an attaching group at one of the atoms of the chain or of a group such as a ring, e.g., benzene ring, part of which is part of the chain. The attaching group is linked to an sbp member or, preferably, contains a functionality to link to an sbp member following attachment of the biotinyl radicals to the chain. Preferably, the bifunctionalized reagent is prepared from smaller molecules containing a lower number of atoms wherein the molecules become covalently bound by virtue of various functionalities mentioned above and in the description of the chain of atoms and the description of the attaching group. For example, carboxylic acid groups, and their nitrogen, e.g., imidate, and sulfur, e.g., isothiocyanate, analogs may be linked to available amino groups as discussed immediately above. The carbonyl of a keto group can be condensed directly with an amino group. An alcohol functionality can react with an anhydride to form a mono ester. The free carboxy group can then be activated by preparing the mixed anhydride and be used for reaction with an amino group. An α-bromoacetamide can be formed from an amino group and used to form a carbon-nitrogen bond to a free amino group.

Thus, another aspect of the present invention is a method of preparing a bis-biotinylated conjugate of an sbp member for use in a specific binding assay. The method comprises the step of reacting the sbp member with a molecule containing two biotinyl radicals connected by a chain of at least 16 atoms as described above. The chain has an attaching group for attaching the molecule to the sbp member.

Another aspect of the present invention is a compound that is a bis-biotin comprising two biotinyl radicals connected by a chain at least 16 atoms in length wherein the chain comprises a functionality reactive with a corresponding functionality of a protein. The functionality and the corresponding functionality are further characterized in that their reaction with each other does not substantially affect the ability of an sbp member to bind to the protein. Preferably, the functionality of the protein is a non-oxocarbonyl and the corresponding functionality is amino. The binding ability is not substantially affected if at least 50%, preferably, at least 70%, of the binding ability of the protein is retained in the compound-protein conjugate.

Another aspect of the present invention is a composition comprising a complex of an avidin and a molecule having two biotinyl radicals connected to one another by a chain at least 16 atoms in length. The chain is conjugated to an sbp member wherein the chain is not part of the sbp member. The biotinyl radicals of the present compounds occupy adjacent biotin binding sites on a single molecule of avidin in substantially the same manner as free biotin molecules.

The compositions of the invention exhibit enhanced stability because they are designed to achieve exclusive bivalent binding, i.e., binding of the two biotinyl radicals to a pair of adjacent binding sites of one molecule of avidin. We have found that compositions having this exclusive bivalent binding have superior stability.

Exclusive bivalent binding may be achieved to the extent required to achieve the enhanced stability of the present compositions when each of the two biotinyl radicals of the particular molecule in question are not sterically prevented from binding to two adjacent biotin-binding sites of a single molecule of avidin in substantially the same orientation relative to the binding sites as two free biotin molecules. By "substantially the same" in this context is meant that the distances between the atoms of the biotinyl radicals and the nearest atoms of the avidin are similar to the corresponding distances between the atoms of biotin and avidin wherein the corresponding distances are usually within at least 80%, preferably within at least 90%, of each other. The biotinyl radical is thus "fully bound by" the biotin-binding site of avidin. Reference is made to FIG. 1 wherein a composition 10 in accordance with the present invention is shown (more fully described in the Examples). The two biotinyl radicals 12 and 14 fully occupy their respective binding sites 16 and 18 of streptavidin 20.

One way of determining whether such a condition can be obtained is to examine models of the molecule in question and of avidin. The examination may be conducted by computer modeling or by molecular models. Computer modeling is preferred. The X-ray structure of crystallized egg white avidin in an active deglycosylated form is reported by Livnah, et al., in *Proc. Natl. Acad. Sci. USA* (1993) 90:3076–3080 and the atomic coordinates and structure factors are deposited in the Protein Data Bank, Chemistry Department, Brookhaven National Laboratory, Upton N.Y. 11973 (reference 2AVI). The X-ray structure of a fragment of the native 159-residue streptavidin chain, incorporating residues 13 through 133, is reported by Weber, et al., *Science* (1989) 243:85 and the atomic coordinates and structure factors are deposited in the Protein Data Bank, Chemistry Department, Brookhaven National Laboratory, Upton N.Y. 11973 (reference 1STP). Weber, et al., state that numerous studies indicate that the above fragment binds biotin with an affinity that is the same as or similar to alternative longer versions of the protein.

One way to determine the strength of binding of the present compositions, and thus to determine whether a particular composition is in accordance with the present invention, is to incubate a solution of less than or equal to $10^{-8}$ M of a 1:1 mole:mole complex of the bisbiotin composition and fully active avidin and $10^{-6}$ M free biotin and measure the rate of release of free bis-biotin. We have found that, when the two biotinyl radicals are connected by a chain that is at least 16 atoms in length having the above elements in accordance with the present invention, exclusive bivalent binding with fully active avidin can be achieved. Less than 1% dissociation of the resulting complexes in the presence of free biotin at 37° C. is observed over 14 days provided the solution is sterile and free of proteases and other materials at least to the extent necessary to avoid deleterious effects on the stability of the composition. In other words, the complexes of the invention remain substantially intact at least during this period of time. Some of the compositions of the present invention can be stored for years without significant dissociation of the bis-biotin compound from the avidin. Such results can be achieved with very dilute solutions either in the presence or absence of free biotin. Any method of sufficient sensitivity can be used to detect the release of free bis-biotin. Normally, the avidin - bis-biotin is separated by precipitation, chromatography, ultrafiltration or the like and the supernatant solution is analyzed for bis-biotin. Analysis can be by radio binding assay, ELISA, fluorescence or luminescence assay, mass spectroscopy, high performance liquid chromatography and the like.

By the term "fully active" avidin is meant avidin that is substantially free from disabled avidin or avidin in which less than all of the biotin binding sites are capable of fully binding biotin. Some avidin preparations may contain as much as 10% of disabled avidin. This disabled avidin binds very weakly to biotin in general. Accordingly, the presence of such disabled avidin will make it appear that dissociation of more than 1%, perhaps as much as 10%, of the complexes of the present bisbiotin compounds and avidin has occurred in the above test. One way to establish whether the avidin preparation contains disabled avidin that results in the above effect is to carry out a second incubation wherein the amount of free biotin is increased such as, for example, by a factor of two. In such an approach the amount of dissociation of the complex will be substantially the same at both concentrations of biotin if the dissociation observed is due to the presence of disabled avidin.

Thus, included within the present invention is a compound comprising two biotinyl radicals covalently bound together by a linking group comprising a chain of atoms at least 16 atoms in length. The chain has an attaching group bound to it. The compound has the characteristic that, when a solution containing (i) less than or equal to $10^{-8}$ M of a 1:1 mole:mole complex of the compound and fully active avidin and (ii) $10^{-6}$ M free biotin is incubated at 37° C. for at least 14 days, the complex exhibits less than 1% dissociation. The attaching group may be conjugated to an sbp member or to a molecule capable of generating electromagnetic radiation.

The compounds of the invention are substantially homogeneous in that they are substantially free of compounds having more than two biotinyl radicals or less than two biotinyl radicals. The present compounds generally contain less than about 50%, usually, less than 90%, preferably, less than 99%, more preferably, less than 99.5%, most preferably, less than 99.9%, of compounds having more or less than two biotinyl radicals.

In one embodiment the present invention can be applied to the labeling of an sbp member. In this approach the bis-biotin - sbp member compound can be mixed with avidin conjugated to a label. Such an approach is convenient when the label is difficult to work with such as an enzyme. Accordingly, in an ELISA assay, for example, an antigen or antibody can be the sbp member of the bis-biotin compound of the invention. This compound can then be incubated with a generic reagent having an enzyme conjugated to avidin. The resulting composition is as stable to multiple washings as a reagent having enzyme covalently linked to the antigen or antibody. Similarly, this approach can be utilized to provide an sbp member bound to a surface or support. Avidin is conjugated to or otherwise bound to a support. Incubation of this avidin reagent with a bis-biotin - sbp member compound of the present invention provides a surface or support to which the sbp member is irreversibly bound. The result is a very stable reagent that does not release free sbp member when the reagent is used.

Accordingly, another aspect of the present invention concerns an improvement in an assay for an analyte, which utilizes a reagent system comprising an avidin reagent and a biotin reagent. The improvement comprises using as the biotin reagent a compound comprising two biotinyl radicals connected by a chain at least 16 atoms in length wherein an sbp member is conjugated to the chain and wherein none of the atoms of the chain is part of the sbp member.

Accordingly, the present compounds and compositions can be used in specific binding assays, utilizing a reagent comprised of an sbp member irreversibly attached to a support or a label. In such an approach avidin is bound to the support or the label and the present composition then binds to the avidin prior to, during or after use of the bis-biotin compound in an assay.

The method of the present invention may be applied to most assays for the determination of an analyte that is an sbp member. In general, a sample suspected of containing an analyte is combined in an assay medium with a binding partner for the analyte. The binding of the binding partner to the analyte, if present, is detected. The binding partner may itself be or be capable of binding to the sbp member of the bis-biotin compound of the invention. The assay can be performed either without separation (homogeneous) or with separation (heterogeneous) of any of the assay components or products.

The present compositions find particular use in homogeneous assays where the reactions can be carried out in solution phase. In these assays any dissociation of a labeled sbp member into free label can reduce the sensitivity of the assay since binding of unlabeled sbp member can compete with binding of labeled sbp member that in turn is related to the presence or amount of analyte to be determined. The stability achieved in the present invention provides numerous advantages for reagents used in assays. For example, a composition in accordance with the present invention does not decompose into component parts, thus releasing, for example, an sbp member component.

Homogeneous immunoassays are exemplified by the EMIT® assay products (Syva Company, San Jose, Calif.) disclosed in Rubenstein, et al., U.S. Pat. No. 3,817,837, column 3, line 6 to column 6, line 64; immunofluorescence methods such as those disclosed in Ullman, et al., U.S. Pat. No. 3,996,345, column 17, line 59 to column 23, line 25; enzyme channeling techniques such as those disclosed in Maggio, et al., U.S. Pat. No. 4,233,402, column 6, line 25 to column 9, line 63; and other enzyme immunoassays such as the enzyme linked immunosorbant assay ("ELISA") are discussed in Maggio, E. T., infra. Exemplary of heterogeneous assays are the radioimmunoassay, disclosed in Yalow, et al., *J. Clin. Invest.* 39:1157 (1960). The above disclosures are all incorporated herein by reference. Another method to which the present invention has application is disclosed in Ullman, et al., U.S. Pat. No. 4,857,453, column 11, line 21 to column 14, line 42, and column 18, line 21 to column 21, line 55, incorporated herein by reference.

Heterogeneous assays usually involve one or more separation steps and can be competitive or non-competitive. A variety of competitive and non-competitive heterogeneous assay formats are disclosed in Davalian, et al., U.S. Pat. No. 5,089,390, column 14, line 25 to column 15, line 9, incorporated herein by reference. In a typical competitive heterogeneous assay a support having an antibody for analyte bound thereto is contacted with a medium containing the sample and analyte analog conjugated to a detectable label such as an enzyme (the "conjugate"). Analyte in the sample competes with the conjugate for binding to the antibody. After separating the support and the medium, the label activity of the support or the medium is determined by conventional techniques and is related to the amount of analyte in the sample.

A typical non-competitive sandwich assay is an assay disclosed in David, et al., U.S. Pat. No. 4,486,530, column 8, line 6 to column 15, line 63, incorporated herein by reference. In this method, an immune sandwich complex is formed in an assay medium. The complex comprises the analyte, a first antibody (monoclonal or polyclonal) that binds to the analyte and a second antibody that binds to the analyte or a complex of the analyte and the first antibody. Subsequently, the immune sandwich complex is detected and is related to the amount of analyte in the sample. The immune sandwich complex is detected by virtue of the presence in the complex of a label wherein either or both the first antibody and the second antibody contain labels or substituents capable of combining with labels.

Sandwich assays find use for the most part in the detection of antigen and receptor analytes. In the assay the analyte is bound by two antibodies specific for the analyte and, thus, the assay is also referred to as the two-site immunometric assay. In one approach a first incubation of unlabeled antibody coupled to a support, otherwise known as the insolubilized antibody, is contacted with a medium containing a sample suspected of containing the analyte. After a wash and separation step, the support is contacted with a medium containing the second antibody, which generally contains a label, for a second incubation period. The support is again washed and separated from the medium and either the medium or the support is examined for the presence of label. The presence and amount of label is related to the presence or amount of the analyte. For a more detailed discussion of this approach see U.S. Pat. Nos. Re 29,169 and 4,474,878, the relevant disclosures of which are incorporated herein by reference.

In a variation of the above sandwich assay the sample in a suitable medium is contacted with labeled antibody for the analyte and incubated for a period of time. Then, the medium is contacted with a support to which is bound a second antibody for the analyte. After an incubation period, the support is separated from the medium and washed to remove unbound reagents. The support or the medium is examined for the presence of the label, which is related to the presence or amount of analyte. For a more detailed discussion of this approach see U.S. Pat. No. 4,098,876, the relevant disclosure of which is incorporated herein by reference.

In another variation of the above, the sample, the first antibody bound to a support and the labeled antibody are combined in a medium and incubated in a single incubation step. Separation, wash steps and examination for label are as described above. For a more detailed discussion of this approach see U.S. Pat. No. 4,244,940, the relevant disclosure of which is incorporated herein by reference.

The present invention has application to all of the above assays. For example, the insolubilized antibody can be formed by combining avidin bound to a support with a bis-biotin compound, having the antibody as the sbp member, in accordance with the invention. This may be done prior to, during or after the immune complexation reactions. Alternatively, or in conjunction therewith, the labeled antibody can also be formed by combining avidin bound to a label with a bis-biotin wherein the sbp member is the second antibody. In another approach the second antibody can be unlabeled and a third antibody for the second antibody can be used. In this approach the third antibody may be the sbp member of the bis-biotin compound of the invention and avidin is bound to a label. When multiple reagents utilize the present concept, the reagents are generally preformed. One advantage of the present invention is that these preformed complexes can be stored together without exchange of the labels that are bound to the separate sbp members.

The present bis-biotin compounds and compositions can be utilized in any of the known situations wherein a mono-biotin reagent is employed. For example, U.S. Pat. No. 4,298,685 (the relevant disclosure of which is incorporated herein by reference) discloses an assay for an analyte that is an antigen, hapten or other biological substance. A sample suspected of containing the analyte is mixed with antibody for the analyte, which is bound to biotin, and with a known amount of the analyte labeled with an enzyme. After the competitive complexation of the antibody with the labeled analyte and the analyte in the sample, avidin immobilized on an inert support is added. The avidin binds to the biotin and causes the complex to be precipitated. After separation of the solid and liquid phases, enzyme activity of one or both is measured, the amount thereof being related to the amount of analyte in the sample. In accordance with the present invention, a bis-biotin compound of the invention can be substituted for the above biotin reagent where the sbp member of the bis-biotin compound is the antibody for the analyte.

Another example is found in U.S. Pat. No. 4,535,057 (the relevant disclosure of which is incorporated herein by reference), which discloses an immunoassay for determining a viral antigen such as herpes simplex. The antigen is immunocaptured by an insoluble matrix to which is bound antibody for the antigen. Then, the matrix is contacted with a biotin reagent wherein biotin is conjugated to a second antibody for the antigen followed by contact with an avidin reagent wherein avidin is conjugated to a detectable label. If the antigen is present, it binds to the antibody on the matrix. The subsequently added biotin reagent binds to the antigen captured on the matrix and the avidin reagent binds to the biotin. The label is detected as an indication of the presence or amount of the antigen. In the improvement provided by the present invention the bis-biotin compound of the present invention can be utilized in place of the biotin reagent of the known assay. In the improved assay the sbp member of the bis-biotin compound is the second antibody for the antigen.

U.S. Pat. No. 4,707,440 (the relevant portions of which are incorporated herein by reference) and its progeny disclose monobiotin and multiple biotin derivatives of (i) chemical entities having a molecular weight of less than about 2000 and of (ii) polymers. Such chemical entities include drugs, naturally occurring physiological compounds, metabolites, pesticides, pollutants, enzyme substrates, the reaction product of an enzyme and its substrate, oligonucleotides and the like. Polymers include polynucleotides, polypeptides and polysaccharides. The disclosed compounds are utilizable in a wide range of applications. For example, the products can be used as detectable products. They can be used in a wide range of in vivo and in vitro therapeutic, diagnostic, imaging and assay techniques. The compounds can be used as detectable molecules wherever biotin/avidin or biotin/streptavidin based pairs of detection systems have been used in the prior art. In accordance with the improvement provided by the present invention, the present bis-biotin compounds may be used in place of those disclosed in U.S. Pat. No. 4,707,440.

The present invention has application in the induced luminescence immunoassay referred to in U.S. Pat. No. 5,340,716 (Ullman, et al.) entitled "Assay Method Utilizing Photoactivated Chemiluminescent Label" ("induced luminescence assay"), which disclosure is incorporated herein by reference. In one approach the assay uses a particle incorporating a photosensitizer and a label particle incorporating a chemiluminescent compound. The label particle is conjugated to an sbp member that is capable of binding to an analyte to form a complex, or to a second sbp member to form a complex, in relation to the presence of the analyte. If the analyte is present, the photosensitizer and the chemiluminescent compound come into close proximity. The photosensitizer generates singlet oxygen and activates the chemiluminescent compound when the two labels are in close proximity. The activated chemiluminescent compound subsequently produces light. The amount of light produced is related to the amount of the complex formed, which in turn is related to the amount of analyte present. By way of illustration as applied to the present invention a particle is employed, which comprises the chemiluminescent compound associated therewith such as by incorporation therein or attachment thereto. The particles are conjugated to avidin. An sbp member that binds to the analyte is provided as part of a bis-biotin compound of the present invention. Incubation of the above reagents yields a single reagent wherein the sbp member is bound to the particle in an irreversible manner. Usually, biotin is then added in an amount sufficient to react with any remaining unoccupied avidin binding sites. A second sbp member that binds to the analyte is part of a second bis-biotin compound in accordance with the present invention. Avidin is conjugated to a second set of particles having a photosensitizer associated therewith. Incubation of these reagents results in a single reagent having the second sbp member bound to the photosensitizer particles in an irreversible manner. Again, biotin may be added to react with unoccupied avidin binding sites. The reaction medium is incubated to allow the particles to bind to the analyte by virtue of the binding of the sbp members to the analyte. Then, the medium is irradiated with light to excite the photosensitizer, which is capable in its excited state of activating oxygen to a singlet state. Because the chemiluminescent compound of one of the sets of particles is now in close proximity to the photosensitizer by virtue of the presence of the analyte, it is activated by the singlet oxygen and emits luminescence. The medium is then examined for the presence and/or the amount of luminescence or light emitted, the presence thereof being related to the presence of the analyte.

The present invention also finds use in agglutination assays employing plastic particles such as latex particles. In a typical agglutination assay of this type, an sbp member is bound to the surface of the plastic particles. This sbp member is capable of binding to an analyte. Usually, the sbp member is an antigen and the analyte is an antibody. The particles are incubated with a medium suspected of containing the analyte. The presence of the analyte causes the particles to agglutinate and the extent of agglutination is measured by known means and related to the presence or amount of the analyte. The present invention can be used to prepare the particles having the sbp member bound thereto. Avidin can be conjugated to the particles, which can be incubated with a bis-biotin compound of the present invention wherein the sbp member of the bis-biotin compound is the sbp member that binds to the analyte. The resulting particles have the sbp member bound thereto in an irreversible manner.

The present compounds and compositions can also be utilized in assays for polynucleotides such as DNA, RNA and so forth. For example, many polynucleotide assays utilize an amplification step to produce a sufficient number of molecules of a polynucleotide, in relation to the presence of a polynucleotide analyte in a sample, so that detection can be facilitated. Such an amplification may involve primer extension. The primer can be designed to be capable of being insolubilized. To this end the primer has biotin attached thereto and avidin is attached to an insoluble support. After the amplification, the reaction medium is contacted with the insolubilized avidin, which is then separated from the reaction medium and washed. A labeled probe that is specific for the target polynucleotide is then added to the insolubilized avidin, which is again washed and examined for the presence of label. The presence of the polynucleotide analyte in the original sample is indicated by the presence of label on the insolubilized avidin. In accordance with the present invention, a bis-biotin compound as described herein may be attached to the primer in place of biotin. Alternatively, the present bis-biotin compounds may be used for forming the labeled probe. Other ways in which the instant bis-biotin compounds can be used in polynucleotide assays will be suggested to those skilled in the art with reference to the present disclosure.

The ability of the present bis-biotin compounds and compositions to withstand heating is particularly attractive for conducting polynucleotide assays. For example, a DNA probe is bound to avidin coated on the surface of a tube by means of a bis-biotin compound in accordance with the present invention wherein the sbp member is the DNA probe. A PCR amplification is carried out in the tube. Any amplicon (anticipated product of the amplification) formed can be allowed to bind to the surface on cooling by virtue of its binding to the DNA probe. If the primer used in the PCR amplification is labeled, the label can be detected by washing the tube and measuring the bound signal from the label. One advantage offered by the present invention is that the DNA probe is bound to the surface by a simple procedure and that the DNA probe is not released on heating.

In another approach two DNA probes are used in a PCR amplification. One of the DNA probes is the sbp member of a bis-biotin compound of the invention, which is bound to avidin conjugated to a fluorescer. The other DNA probe is the sbp member of another bis-biotin compound of the invention, which is bound to avidin conjugated to an energy acceptor. Both DNA probes can be present in the amplification because the above reagents are thermally stable. After the PCR amplification is completed to the desired point and the reaction mixture is cooled to allow binding of the probes, fluorescence signal is measured to determine if amplicon has been formed.

For assays conducted using the bis-biotin compounds of the present invention, the assay is normally carried out in an aqueous buffered medium at a moderate pH, generally that which provides optimum assay sensitivity. The aqueous medium may be solely water or may include from 0 to 20 volume percent of a cosolvent. The pH for the medium will usually be in the range of 4 to 11, more usually in the range of 5 to 10, and preferably in the range of 6.5 to 9.5. The pH will usually be a compromise between optimum binding of the binding members of any specific binding pairs, optimum binding of the bis-biotin compounds with avidin in accordance with the present invention, and the pH optimum for other reagents of the assay such as members of the signal producing system.

Various buffers may be used to achieve the desired pH and maintain the pH during the determination. Illustrative buffers include borate, phosphate, carbonate, TRIS and barbital. The particular buffer employed is not critical, but in an individual assay one or another buffer may be preferred.

Moderate to relatively high temperatures can be employed for carrying out an assay. The temperatures can be constant or varying and will depend on the type of assay conducted and the reagents utilized. Incubation temperatures will normally range from 5 to 100° C., more usually from 20 to 95° C. Temperatures during measurements will generally range from 5 to 100° C., more usually from 20 to 95° C.

The concentration of analyte that may be assayed will generally vary from $10^{-5}$ to $10^{-7}$ M, more usually from $10^{-6}$ to $10^{-15}$ M. Considerations, such as whether the assay is qualitative, semiquantitative or quantitative (relative to the amount of analyte present in the sample), the particular detection technique and the concentration of the analyte, and optimization of the binding between the present bis-biotin compounds and avidin normally determine the concentrations of the various reagents.

The concentrations of the various reagents in the assay medium is generally determined by the concentration range of interest of the analyte. However, the final concentration of each of the reagents is normally determined empirically to optimize the sensitivity of the assay over the range. That is, a variation in concentration of analyte which is of significance should provide an accurately measurable signal difference.

While the order of addition may be varied widely, there will be certain preferences depending on the nature of the assay. In one order of addition, which is the simplest order, all the materials are added simultaneously and determination is made of the effect that the assay medium has on the signal as in a homogeneous assay. Alternatively, the reagents can be combined wholly or partially sequentially. Optionally, an incubation step may be involved subsequent to each addition, generally ranging from 30 seconds to 6 hours, more usually from 1 minute to 1 hour.

Another aspect of the present invention is a kit comprising in packaged combination an avidin reagent and a compound consisting of a bis-biotin comprised of two biotinyl radicals connected by a chain at least 16 atoms in length. The bis-biotin is conjugated to an sbp member wherein the chain is not part of the sbp member. The avidin reagent can comprise avidin bound to a support.

To enhance the versatility of the subject invention, the kit reagents can be provided in packaged combination, in the same or separate containers, in liquid or lyophilized form so that the ratio of the reagents provides for substantial optimization of the method and assay. The reagents may each be in separate containers or various reagents can be combined in one or more containers depending on the cross-reactivity and stability of the reagents.

The kit can further include other separately packaged reagents for conducting an assay such as additional sbp members, ancillary reagents such as additional sps members, e.g., an ancillary enzyme substrate, and so forth. The relative amounts of the various reagents in the kits can be varied widely to provide for concentrations of the reagents which substantially optimize the reactions that need to occur during the present method and to further substantially optimize the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. The kit can further include a written description of a method in accordance with the present invention as described above.

EXAMPLES

The invention is demonstrated further by the following illustrative examples. Parts and percentages herein are by weight unless otherwise indicated. Temperatures are in degrees Centigrade (°C.).
Materials and Source
  Aldrich Chemicals
  2,2'-(ethylene dioxy)bis(ethylamine)
  Di-tert-butyl dicarbonate
  5-aminovaleric acid
  benzyl chloroformate
  N,N'-dicyclohexyl carbodiimide
  biotin
  N-hydroxy succinimide
  Dimethyl formamide sure/seal bottle
  10% Palladium on activated carbon
  triethylamine
  Boehringer Mannheim
  Digoxigenin-3-0-methylcarbonyl-ε-aminocaproic acid-N-hydroxysuccinimide ester
  Mallinckrodt Chemicals
  ethyl ether anhydrous
  methanol
  tetrahydrofuran anhydrous (distilled from Na)
  hydrochloric acid
  dichloromethane
  sodium hydroxide
  sodium chloride
  sodium sulfate anhydrous
  sodium carbonate

EXAMPLE 1

Preparation of 1,10-diaza-13,13-dimethyl-11-oxo-4,7,12-trioxatetra-decane 3 from 2,2'-(ethylene dioxy)bis (ethylamine) 1 and di-tert-butyl dicarbonate 2.

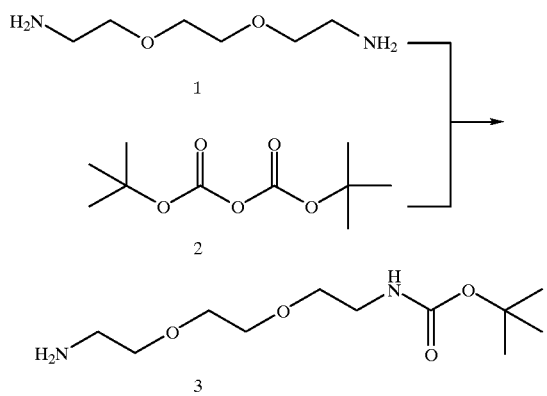

Into a one-liter Erlenmeyer flask equipped with a magnetic stirring bar was placed 100 g (0.68 mols) of 2,2'-(ethylenedioxy)bis(ethylamine) 1 and 500 mL dichloromethane. The solution was cooled with an ice bath to 5° C. with vigorous stirring. Then, a solution of 50 g (0.23 mols) of Di-tert-butyl dicarbonate 2 in 200 mL dichloromethane was introduced dropwise over a period of 1 hour. The reaction was warmed to room temperature and stirring was continued for an additional hour. The solution was placed in a 2-liter separatory funnel and extracted 3 times with 600 mL water. The monoprotected diamine was extracted from the organic phase with 6×250 mL 1 N HCL. The pooled acidic extracts were immediately brought to pH 10.0 with 5 N NaOH and saturated with solid sodium chloride. The product was extracted with 4 times with 500 mL dichloromethane, pooled, dried over $Na_2SO_4$, filtered through glass wool plug and concentrated on a rotary evaporator.

The viscous, colorless oil was further concentrated under vacuum 0.8 mm, yielding 47 g of N-tboc-1,10-diaza-4,7-dioxadecane. By thin layer chromatographic (tlc) analysis and nuclear magnetic resonance (NMR) spectroscopy, no further purification was necessary. Tlc analysis: 250μ Analtech silica gel GF, 3:7 methanol:dichloromethane, Rf ≈0.27. Sprayed with 1.5% ninhydrin in ethanol and visualized with heating. Formula weight $C_{11}H_{24}N_2O_4$ 248.32. Yield 82% based on dicarbonate, 30% based on diamine.

EXAMPLE 2

Preparation of N-[3,6,11-trioxa-10-oxo-9-aza-12,12-dimethyltridecyl]-3,5 dinitrobenzamide 5 from 3 and 3,5-dinitrobenzoylchloride 4.

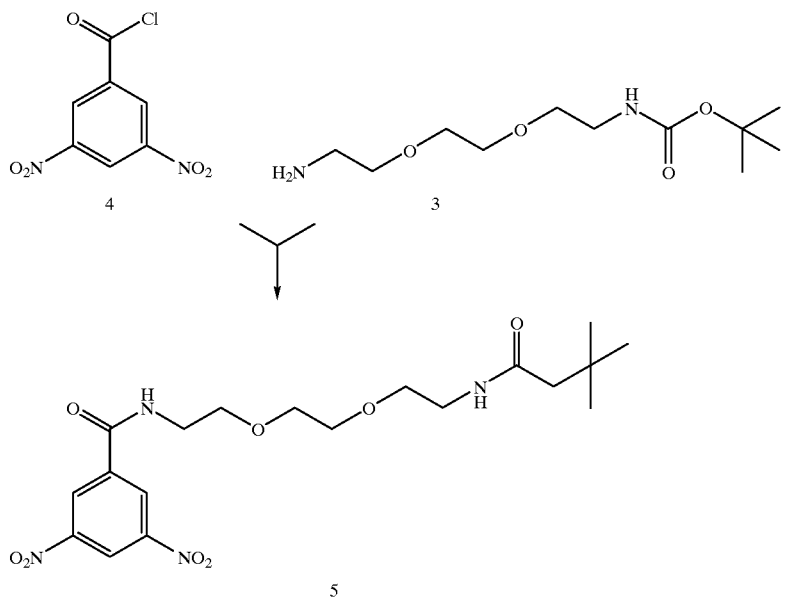

Into a one-liter Erlenmeyer flask equipped with a magnetic stirring bar were placed 22.3 g (0.09 mols) of 3, 10.1 g (0.10 mols) triethylamine and 200 mL of anhydrous tetrahydrofuran. To this stirring solution was added dropwise 20 g (0.09 mols) of 3,5-dinitrobenzoyl chloride dissolved in 200 mL of anhydrous tetrahydrofuran over 30 minutes. Upon completion of addition, the reaction mixture was stirred for 1.5 hours at room temperature and then was concentrated on rotary evaporator, and the crude residue was purified by extraction. The residue was dissolved in 400 mL dichloromethane and 250 mL water was added. This mixture was placed into a separatory funnel and was extracted with the following: 2×250 mL 0.2 N-hydrochloric acid, 2×100 mL 0.1 M sodium carbonate and 1×200 mL water.

The organic phase was dried over $Na_2SO_4$, filtered and the filtrate was concentrated on a rotary evaporator. The oil was then further dried under higher vacuum 0.6 mm, 50° C. water bath.

The light brown very viscous oil 5 afforded 36.7 g (97%) of product. $C_{18}H_{26}N_4O_9$ Formula weight 441.4. Tlc analysis: Analtech 250μ silica gel GF; eluant, ethyl acetate; Rf≈0.77; visualized with UV lamp.

EXAMPLE 3

Preparation of N-benzyloxycarbonyl-5-amino-pentanoic acid 8 from 5-aminovaleric acid 6 and benzylchloroformate 7.

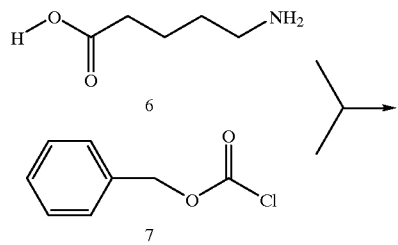

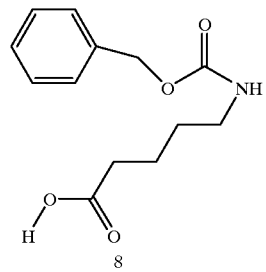

Into a one-liter round bottom flask equipped with a magnetic stirring bar was placed 400 mL of water followed by 20 g (0.15 mols) of solid 5-aminovaleric acid 6 and 40 g (0.38 mols) of sodium carbonate.

After all the 5-aminovaleric acid 6 had dissolved, the solution was cooled in an ice bath at 5–10° C. Then, with vigorous stirring, a solution of 29.7 g benzyl chloroformate 7 in 100 mL anhydrous tetrahydrofuran was added dropwise over a 20 minute period. Upon completion of addition, the solution was stirred at room temperature for an additional 2 hours.

The reaction mixture was concentrated on a rotary evaporator to remove most of the tetrahydrofuran. Then, the pH of the solution was adjusted to 5.0 with concentrated hydrochloric acid. The white precipitate was vacuum filtered through Buchner funnel, washed with 400 mL water, and air dried.

The product was further dried for 16 hours under vacuum with heating (0.8 mm, 80° C.). The product 8 was obtained in a 33 g (91%) yield. Formula weight $C_{13}H_{17}N_1O_4$ 251.2.

EXAMPLE 4

Two step preparation of N-[3,6,11,trioxa-10-oxo-9aza-12,12-dimethyl tridecyl]-3,5-bis[(5-aza-1,6-dioxo-7-oxa-8-phenyl octyl)amino]benzamide 11 by reduction of 5 to the diamine 9 followed by acylation with N-benzyloxycarbonyl-5-aminopentanoic anhydride 10.

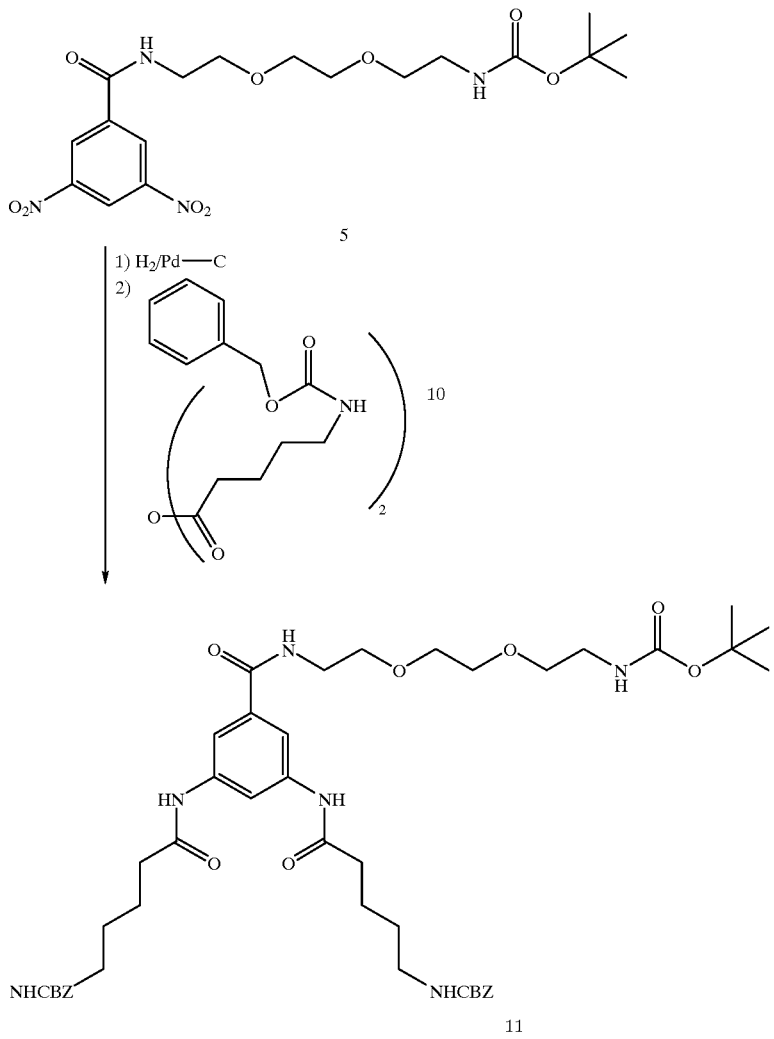

Into a 500 mL Parr hydrogenation vessel was placed 1.32 g (0.003 mols) of 5 in 40 mL of absolute ethanol. A stream of argon was introduced and 0.50 g 10% Palladium on carbon was added to the solution. The mixture was placed on the Parr hydrogenation and evacuated (house vacuum) and purged with nitrogen twice. The mixture was subjected to 50 psi hydrogen atmosphere at room temperature with shaking for 2 hours. The catalyst was removed by filtration through medium fritted disc Buchner funnel, washed with ethanol and the filtrate was concentrated on a rotary evaporator. The residue was further dried under higher vacuum with heating for 4 hours (0.5 mm, 60° C.). No further purification of the diamine product was necessary by tlc analysis. 250p Analtech silica gel GF plate; eluant 1:9 methanol:dichloromethane; Rf≈0.45; visualized with UV lamp and cerium sulfate spray (0.25N cerium IV sulfate in 2N sulfuric acid).

A dried (0.8 mm, 80° C., 16 hr) 6 g (0.024 mols) portion of N-benzyloxycarbonyl (CBZ)-aminovaleric acid 8 and 2.4 g (0.012 mols) of N,N-dicyclohexyl carbodiimide were combined in a 250 mL round bottom flask followed by 60 mL of anhydrous tetrahydrofuran. The reaction solution was stirred with a magnetic bar for 5 hrs at room temperature. The precipitated N,N-dicylohexylurea was removed by vacuum filtration through medium fritted disc Buchner funnel. The white solid was washed with 30 mL anhydrous tetrahydrofuran.

To the previously prepared diamine 9 in a 250 mL round bottom flask equipped with magnetic bar and calcium chloride drying tube was added 2.73 g (0.03 mols) triethylamine and 75 mL anhydrous tetrahydrofuran. The mixture was then stirred at room temperature and the above prepared anhydride solution was added dropwise over 15 minutes. The reaction mixture was left stirring at room temperature for approximately 16 hrs. Tlc analysis: Analtech 250μ silica gel GF plate, eluant 1:1:8 methanol/hexane/dichloromethane; Rf≈0.80; visualized with UV lamp and cerium sulfate spray (0.25N cerium IV sulfate in 2N sulfuric acid). The diamine and monoacylation intermediate appeared as brown spots with cerium spray.

The reaction mixture was concentrated on a rotary evaporator and the residue was dissolved in 250 mL ethyl acetate and 200 mL water. The two layers were separated in a separatory funnel. The organic layer was extracted successively with 200 mL water, two 200 mL 1N sodium bicarbonate, two 200 mL 3.6% hydrochloric acid and one 200 mL of brine. The organic layer was dried over anhydrous sodium sulfate. The solvent was removed by decanting from drying agent. The solvent was removed on a rotary evaporator. The residue was purified by chromatography on 12-12×20 cm Analtech 1000μ silica gel CF plates using 1:1:8 methanol/hexane/dichloromethane as the eluant.

The bands containing diacylated product were isolated and pooled. The product was extracted from the absorbent with 3:7 methanol/dichloromethane and the filtrate was concentrated on a rotary evaporator. The colorless oil was further concentrated under reduced pressure to afford 1.8 g (72%) of di-CBZ product 11.

The reaction of the anhydride 10 with the diamine 9 required an excess of acid 8. Difficulty of purification with unreacted diamine 9 present was more than likely due to the similar Rf values between 9 and product 11.

An alternative approach involved activation of 8 to an acid chloride using oxalyl chloride; 1.13 g (0.045 mols) of 8 was placed in a 100 ml round bottom flask equipped with a stirring bar and calcium chloride drying tube followed by 25 ml of anhydrous dichloromethane. To the stirring suspension was added 1.26 g (0.01 mols) of oxalyl chloride, and solution was stirred for 3 hours at room temperature. The solution, which was at this time homogeneous, was concentrated on a rotary evaporator and then was dried further under higher vacuum (0.8 mm, 16 hr.). The oil was taken up with dichloromethane and added in place of the anhydride 10 to the above diamine 9.

EXAMPLE 5
Preparation of the biotinyl-N-hydroxysuccinimide ester 14.

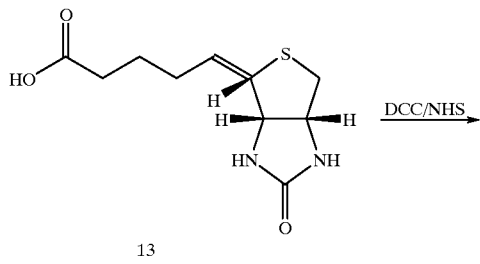

-continued

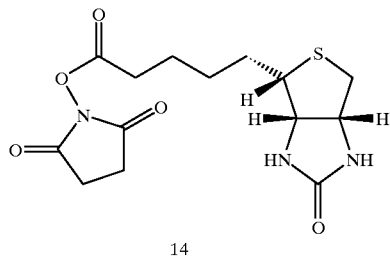

To a stirring solution of 3 g (0.0123 mols) of (+) biotin 13 dissolved in 50 mL of anhydrous dimethylformamide at 90° was added 1.5 g (0.013 mols) N-hydroxysuccinimide. The stirring solution was allowed to cool to room temperature. This was followed by the addition of 2.68 g (0.013 mols) of N',N-dicyclohexylcarbodiimide in 25 mL of anhydrous dimethylformamide. The solution was stirred at room temperature overnight.

After 16 hours, the reaction solution was vacuum filtered through a medium fritted disc Buchner funnel. The solid white dicyclohexylurea was washed with 25 mL anhydrous dimethylformamide. The filtrate was concentrated on a rotary evaporator using a vacuum pump with a water bath at 40° C. to a volume of 50 mL solvent. A small amount of N',N-dicyclohexylurea appeared in the round bottom flask and was filtered using a medium fritted disc Buchner funnel. The filtrate was diluted with swirling with 500 mL of anhydrous ethyl ether. The white precipitate that formed was collected by vacuum filtration, washed with 100 mL ethyl ether and air dried. The reaction afforded a 3.9 g (95%) of biotinyl-N-hydroxysuccinimide ester 14.

EXAMPLE 6
A two step preparation of N-[3,6,11-trioxa-10-oxo-9-aza-12,12-dimethyltridecyl]-3,5-bis[5-biotinoylamino-1-oxo pentyl)amino]benzamide 15 by hydrogenolysis and biotinylation of 11.

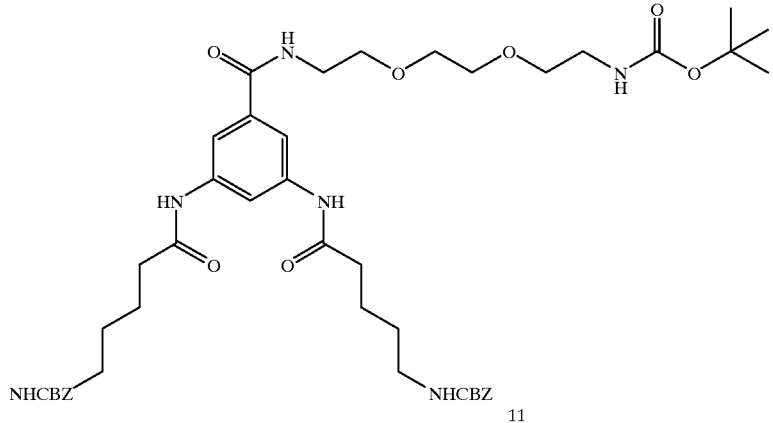

-continued

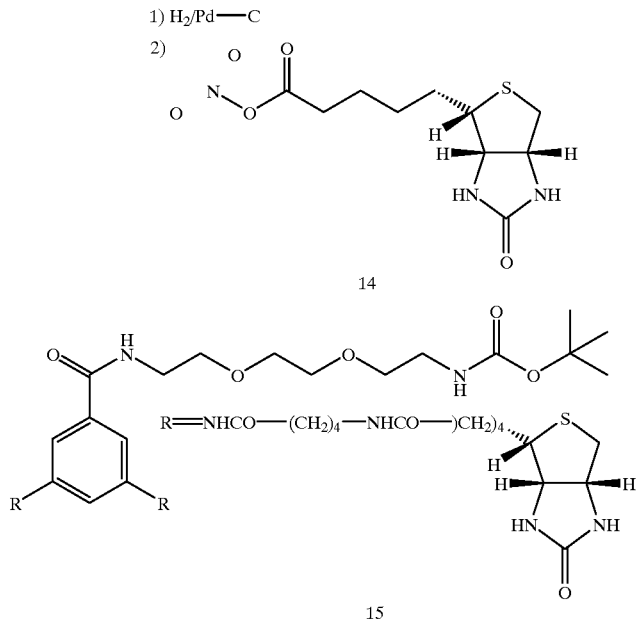

Into a 500 mL Parr hydrogenation vessel was placed 790 mg (0.93 mmols) of 11 dissolved in 35 mL absolute ethanol. Under a flow of argon, the vessel was charged with 500 mg of 10% Palladium on activated carbon. The mixture was placed on a Parr hydrogenation and the air was purged with nitrogen. Then, the vessel was evacuated and the contents were placed under 50 psi hydrogen atmosphere. The reaction mixture was shaken at room temperature for 2 hours.

The catalyst was removed by vacuum filtration through a medium fritted disc Buchner funnel. The filtrate was concentrated on a rotary evaporator and then further under higher vacuum (0.5 mm at 60° C.) for 5 hours yielding an oil.

To a stirring solution of 480 mg (0.828 mmols) of the diamine obtained above, 300 µL triethylamine and 25 mL of anhydrous dimethylformamide in 250 mL round bottom flask was added 566 mg (1.66 mmols) of biotinyl N-hydroxysuccinimide ester 14. The solution was left stirring at room temperature for 4 hours. Tlc analysis: Analtech 250µ silica gel GF plate. A 20 µl aliquot of the reaction mixture was concentrated under vacuum. The residue was dissolved 1:9 methanol/dichloromethane and applied to the tlc plate. The plate was eluted with 1:9 methanol/dichloromethane. The product was visualized with UV lamp and spray reagent (1:1 (v/v) of 2% sulfuric acid/0.2% p-dimethylamino-cinnamaldehyde in ethanol). The product had an Rf≈0.46.

The reaction mixture was concentrated to 10 mL on a rotary evaporator using a vacuum pump at 40° C. Then, the solution was added dropwise to a vortexing 100 mL of a saturated sodium chloride solution. The residual material was taken up with 10 mL methanol and added to the above sodium chloride solution. The product precipitated and was centrifuged at 3000 rpm for 5 minutes. The solid residue was dried under vacuum. The dried crude product was purified using preparative thin layer chromatography. The solid was dissolved in minimum 2:8 methanol/dichloromethane applied to 9-20×20 cm 1000µ Analtech silica gel CG plates and the eluant was 2:8 methanol/dichloromethane. The appropriate bands were visualized with a UV lamp and pooled. The product was extracted from the absorbent with 3:7 methanol/dichloromethane and the filtrate was concentrated on a rotary evaporator. The residue was dissolved in 2:8 methanol/dichloromethane placed in a vial and concentrated at 40° C. under a stream of argon. The product was further dried under vacuo with heating (0.5 mm, 80° C. over $P_2O_5$). The product 15 appeared as a white foam with yield of 650 mg (75%).

EXAMPLE 7

Two step preparation of N-[(9,16-diaza-18(3-0-digoxigenin)-3,6-dioxa-10,17-dioxo-octa decyl)]-3,5-bis [5-biotinyolamino-1-oxopentyl)amino]benzamide 17 by removal of the t-Boc protecting group of 15 and acylation with digoxigenin hapten NHS ester 16.

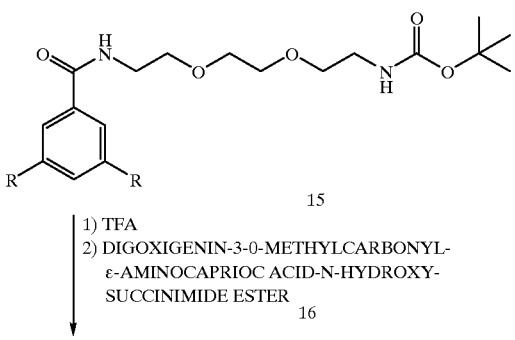

35
-continued

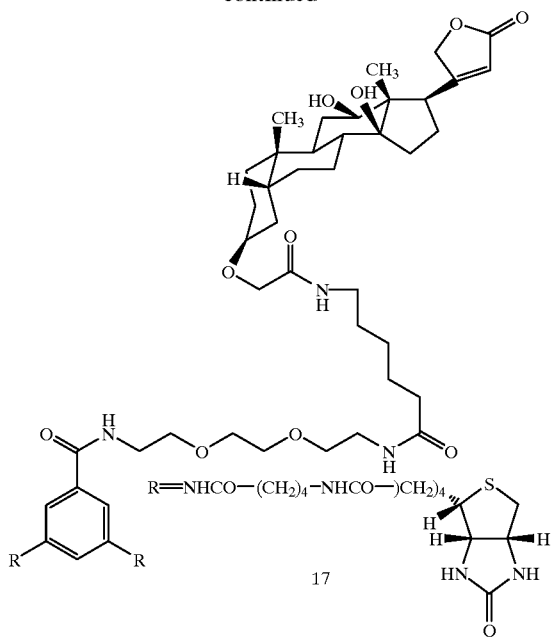

17

Removal of t-Boc protecting group

Into a 50 mL round bottom flask equipped with a calcium chloride drying tube was placed 34 mg (0.034 mmols) of 15 (previous dried 0.8 mm, 80° C., 16 hours). Then, a 10 mL 1:1 solution of trifluoroacetic acid/dichloromethane was added. The reaction mixture was swirled until all solid had dissolved and left for 10 minutes at room temperature. Then, without heating, the reaction mixture was concentrated on a rotary evaporator.

The following procedure was performed to remove excess trifluoroacetic acid from crude product. The residue was suspended in 15 mL dichloromethane and 20 mL n-heptane added to the solution. The mixture was concentrated on a rotary evaporator and then further dried under vacuum 0.8 mm with heating 80° C. for 16 hours.

Coupling of bisbiotin amine to a Digoxin hapten 16.

To the above dried residue was added a magnetic stirring bar, 10 mL anhydrous dimethylformamide and 100 μL triethylamine. The pH of the solution was determined to be >9 by applying a 20 μL aliquot to wetted pH paper. Then, 20 mg (0.03 mmols) of solid digoxigenin 3-0-methylcarbonyl-ε-aminocaproic acid -N-hydroxy succinimide ester 16 was added at one time. The reaction mixture was stirred at room temperature for 4 hours.

The majority of the solvent was removed on a rotary evaporator with heating at 40° C. This left a syrup, which was taken up with methanol and added drop wise to a vortexing solution of 30 mL water saturated brine in a glass centrifuge tube. The precipitated product was centrifuged 5 minutes at 3000 rpm and supernatant decanted. The residue was dried under vacuum. Then, the crude product was purified by preparative thin layer chromatography. The product was dissolved in 2:8 methanol/dichloromethane and applied to 8-20×20 cm Analtech 1000μ silica gel GF plates and was eluted with 2:8 methanol/dichloromethane. The major UV active bands (Rf ≈0.5) were combined and product was extracted from absorbent with 2.5:7.5 methanol/dichloromethane by vacuum filtration. The filtrate was concentrated on a rotary evaporator. The residue was dissolved in 2:8 methanol/dichloromethane and placed into a 2 dram vial. The solvent was removed under a stream of argon. Then, the product was further dried in a Abderhalden apparatus with heating under vacuum for 16 hours (0.8 mm, 80° C. over $P_2O_5$). The product 17 was obtained in 38 mg (86%) as a solid foam. Tlc analysis: Analtech 250μ silica gel GF, eluant 2:8 methanol/dichloromethane (Rf≈0.49). The product was visualized with either of the following: a UV lamp, cerium sulfate spray (0.25N cerium IV sulfate in 2N sulfuric acid) and biotin spray (1:1 (v/v) of 2% sulfuric acid/0.2% p-dimethyl aminocinnimaldehyde in ethanol).

EXAMPLE 8

Assay for Digoxin

Abbreviations, Materials and Equipment

Sav—streptavidin

ELISA—enzyme linked immunosorbent assay as described in "Enzyme-Immunoassay," Edward T. Maggio, CRC Press, Inc., Boca Raton, Fla. (1980)

TRIS—Tris(hydroxymethyl)aminomethane-HCl (a 10× solution) from BioWhittaker, Walkersville, Md., or from J.T. Baker (cat. #4099-02).

sec—seconds hr—hours min—minutes

RLU—relative light units

Ab—antibody

NHS—N-hydroxysuccinimide

EDAC—1-ethyl-3-(3-dimethylaminopropyl) carbodiimide hydrochloride rpm—rotations per min ACN—acetonitrile MAbDIG—anti-digoxin monoclonal antibody $NaBH_3CN$—sodium cyanoborohydride CMO—carboxymethoxylamine hemihydrochloride NaOAc—sodium acetate SAV—streptavidin DMF—dimethylformamide TEA—triethylamine Sens—sensitizer Dextran T-500 from Pharmacia, catalog #17-0320-02.

Sodium hydroxide from Mallinckrodt AR (lot 7707 KMRT).

Water (deionized) from a Millipore Filtration Unit.

Minikros Lab System (Microgon Inc. cat. #SYLS 12101N) and Minikros tangential flow modules (M25S 300 01N, M25S 600 01N, M21M-300-01N) were also from Microgon Inc. Laguna Hills, Calif.

EDTA $Na_2$—Disodium ethylene diamine tetraacetic acid, from Sigma (cat. #E4884).

Bovine Serum Albumin (BSA) was from Sigma (cat. #A7888).

Gentamicin sulfate was from GIBCO (cat. #15750-011).

Kathon was from Rohm & Haas, part #5A033, lot C1.

NaOH (pellets), 0.1N NaOH, HCl (conc.), $H_2SO_4$ (conc.) and 0.1N HCl were from Mallinckrodt (AR. grade).

Boric Acid ($H_3BO_3$, granular), acetic acid (glacial, AcOH) and sodium acetate (NaOAc) were obtained from Mallinckrodt (AR grade).

Streptavidin was purchased from Aaston, Inc., (cat. #1 STA-1G-D), or Boehringer Mannheim (cat. #1520679103).

Sodium cyanoborohydride, $NaCNBH_3$ (cat. #15,615-9), sodium borohydride,

CMO—carboxymethoxylamine hemihydrochloride, (cat. #C1,340-8) from Aldrich.

Tween-20—(Surfact-Amps 20) were purchased from Pierce.

Particle size was determined by dynamic light scattering on a Nicomp (model 370).

Buffer A—0.1M, pH 5.0 acetate buffer for hydrazone formation and reductive aminations; 0.2 M solution of sodium acetate (16.4 g) dissolved in 2.0 L of water combined with 0.2 M acetic acid to pH 5.0; diluted with an equal volume of water to give 0.1 M acetate buffer at pH 5.0.

Buffer B—protein free buffer for washing streptavidin coated beads; 121.1 g of TRIS, 175.3 g of NaCl, 93.0 g of EDTA $Na_2.2H_2O$ and 10.0 g of dextran T-500 in 10.0 L of water; adjusted to pH to 8.3 with concentrated HCl.

Buffer C—121.1 g of TRIS (0.1M), 175.3 g of NaCl (0.3M), 93.0 g of EDTA $Na_2.2H_2O$ (25 mM), 10.0 g of Dextran T-500 (0.1%), 31.25 ml of HBR-1 (from Scantibodies Laboratory Inc., Los Angeles, Calif.) (1/320), 10.0 g of RIA grade BSA (0.1%), 5 mL of Kathon (0.05%) and 20 mL of Gentamicin sulfate (0.01%) in 10.0 L of water; adjusted to pH to 8.3 with concentrated HCl.

Monoclonal antibodies were obtained by somatic cell hybridization techniques such as the standard techniques of Köhler and Milstein, *Nature* 265:495–497,1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3–46 (1981). Samples of an appropriate immunogen preparation were injected into an animal such as a mouse, e.g., Balb/c mouse, and, after a sufficient time, the animal was sacrificed and spleen cells obtained after a suitable period of time. Alternatively, the spleen cells of a non-immunized animal can be isolated and directly sensitized to the immunogen in vitro. The spleen cell chromosomes encoding the base sequences for the desired immunoglobins were compressed by fusing the spleen cells, generally in the presence of a non-ionic detergent, for example, polyethylene glycol, with a myeloma cell line. The resulting cells, which include fused hybridomas, were allowed to grow in a selective medium, such as HAT-medium, and the surviving immortalized cells were grown in such medium using limiting dilution conditions. The cells were grown in a suitable container, e.g., microtiter wells, and the supernatant was screened for monoclonal antibodies having the desired specificity. A number of screening techniques were employed such as, for example, ELISA screens. Selected fusions were then recloned.

Various techniques exist for enhancing yields of monoclonal antibodies, such as injection of the hybridoma cells into the peritoneal cavity of a mammalian host, which accepts the cells, and harvesting the ascites fluid. Where an insufficient amount of the monoclonal antibody collects in the ascites fluid, the antibody is harvested from the blood of the host. Alternatively, the cell producing the desired antibody can be grown in a hollow fiber cell culture device or a spinner flask device, both of which are well known in the art. Various conventional ways exist for isolation and purification of the monoclonal antibodies from other proteins and other contaminants (see Köhler and Milstein, supra).

Silicon tetra-t-butyl phthalocyanine was prepared as follows: Sodium metal, freshly cut (5.0 g, 208 mmol), was added to 300 mL of anhydrous ether in a two-liter, 3-necked flask equipped with a magnetic stirrer, reflux condenser, a drying tube and a gas bubbler. After the sodium was completely dissolved, 4-t-butyl-1,2-dicyanobenzene (38.64 g, 210 mmol, from TCI Chemicals, Portland Oreg.) was added using a funnel. The mixture became clear and the temperature increased to about 50° C. At this point a continuous stream of anhydrous ammonia gas was introduced through the glass bubbler into the reaction mixture for 1 hr. The reaction mixture was then heated under reflux for 4 hr. while the stream of ammonia gas continued. During the course of the reaction, as solid started to precipitate. The resulting suspension was evaporated to dryness (house vacuum) and the residue was suspended in water (400 mL) and filtered. The solid was dried (60° C., house vacuum, $P_2O_5$). The yield of the product (1,3-diiminoisoindoline, 42.2 g) was almost quantitative. This material was used for the next step without further purification. To a one-liter, three-necked flask equipped with a condenser and a drying tube was added the above product (18 g, 89 mmol) and quinoline (200 mL, Aldrich Chemical Company, St. Louis Mo.). Silicon tetrachloride (11 mL, 95 mmol, Aldrich Chemical Company) was added with a syringe to the stirred solution over a period of 10 min. After the addition was completed, the reaction mixture was heated to 180–185° C. in an oil bath for 1 hr. The reaction was allowed to cool to room temperature and concentrated HCl was carefully added to acidify the reaction mixture (pH 5–6). The dark brown reaction mixture was cooled and filtered. The solid was washed with 100 mL of water and dried (house vacuum, 60° C., $P_2O_5$). The solid material was placed in a 1-liter, round bottom flask an concentrated sulfuric acid (500 mL) was added with stirring. The mixture was stirred for 4 hr at 60° C. and was then carefully diluted with crushed ice (2000 g). The resulting mixture was filtered and the solid was washed with 100 mL of water and dried. The dark blue solid was transferred to a 1-liter, round bottom flask, concentrated ammonia (500 mL) was added, and the mixture was heated and stirred under reflux for 2 hr, was cooled to room temperature and was filtered. The solid was washed with 50 mL of water and dried under vacuum (house vacuum, 60° C., $P_2O_5$) to give 12 g of product silicon tetra-t-butyl phthalocyanine as a dark blue solid. 3-picoline (12 g, from Aldrich Chemical Company), tri-n-butyl amine (anhydrous, 40 mL) and tri-n-hexyl chlorosilane (11.5 g) were added to 12 g of the above product in a one-liter, three-necked flask, equipped with a magnetic stirrer an a reflux condenser. The mixture was heated under reflux for 1.5 hr an then cooled to room temperature. The picoline was distilled off under high vacuum (oil pump at about 1 mm Hg) to dryness. The residue was dissolved in $CH_2Cl_2$ and purified using a silica gel column (hexane) to give 10 g of pure product di-(tri-n-hexylsilyl)-silicon tetra-t-butyl phthalocyanine as a dark blue solid. (MS: $[M-H]^+$ 1364.2, absorption spectra: methanol: 674 nm ($\epsilon$180,000): toluene 678 nm, $^1H$ NMR (250 MHz, $CDCl_3$): $\delta$: −2.4 (m, 12H), −1.3 (m, 12H), 0.2–0.9 (m, 54H), 1.8 (s, 36H), 8.3 (d, 4H) and 9.6 (m, 8H) was consistent with the above expected product.

Sens-beads—The sensitizer beads were prepared by placing 600 mL of carboxylate modified beads (Seradyn, lot #2428) in a three-necked, round-bottom flask equipped with a mechanical stirrer, a glass stopper with a thermometer attached to it in one neck, and a funnel in the opposite neck. The flask had been immersed in an oil bath maintained at 94+/−1° C. The beads were added to the flask through the funnel in the neck and the bead container was rinsed with 830 mL of ethoxyethanol, 1700 mL of ethylene glycol and 60 mL of 0.1N NaOH and the rinse was added to the flask through the funnel. The funnel was replaced with a 24-40 rubber septum. The beads were stirred at 765 rpm at a temperature of 94+/−1° C. for 40 min.

Silicon tetra-t-butyl phthalocyanine (10.0 g) was dissolved in 300 mL of benzyl alcohol at 60+/−5° C. and 85 mL was added to the above round bottom flask through the septum by means of a syringe heated to 120+/−10° C. at a rate of 3 mL per min. The remaining 85 mL of the phthalocyanine solution was then added as described above. The syringe and flask originally containing the phthalocyanine was rinsed with 40 mL of benzyl alcohol and transferred to round-bottom flask. After 15 min 900 mL of deionized water and 75 mL of 0.1N NaOH was added dropwise over 40 min. The temperature of the oil bath was allowed to drop slowly to 40+/−10° C. and stirring was then discontinued. The beads were then filtered through a 43 micron polyester filter and subjected to a Microgon tangential flow filtration apparatus (Microgon Inc., Laguna Hills, Calif.) using ethanol:water, 100:0 to 10:90, and then filtered through a 43 micron polyester filter. The beads were stored at 33 mg/mL in 10% ethanol/water. The size of the beads was 215±7% in water with a dye content of 106 mM.

Streptavidin coated Sens-beads were prepared as follows:

Streptavidin from Aaston was a lyophilized white powder containing streptavidin, potassium phosphate, sodium chloride and lactose. The lactose was removed by dialysis against 10 mM $Na_2HPO_4/NaH_2PO_4$ at pH 7.0. A solution of streptavidin at 10–12 mg/mL (75–62.5 mL) was prepared in Buffer A (pH 5.0, 0.2M).

Aldehyde groups were introduced onto the surface of the Sens-beads prepared as described above. See, for example, U.S. Pat. No. 4,264,766 particularly at column 7, lines 18–42, and column 8, line 63, to column 9, line 25, and U.S. Pat. No. 4,801,504 particularly at column 6, lines 42–50, the relevant portions of both of the above patents being incorporated herein by reference thereto.

A 20 mg/mL solution of aldehyde Sens-beads containing Tween-20 (75 mL) was prepared. The beads were added slowly to the streptavidin solution, prepared above, contained in a 250 mL glass bottle with gentle stirring. A fresh solution of $NaCNBH_3$ in water was prepared and added to the reaction mixture. The final concentration of the reaction mixture was at least 10 mg/mL in beads, 5 mg/mL in streptavidin, 1.0 mg/mL in $NaCNBH_3$ and 0.1% in Tween-20. The pH of the reaction mixture was adjusted to 5.0. The bottle was shielded from light and shaken at 100–150 rpm at 37° C. for 48–60 hr. The resulting beads were treated to block remaining free aldehyde groups. See, for example, Margel, S., *J. Chromatogr.* (1989) 462:177–189. The beads were then subjected to ultrafiltration on the Microgon (0.05, pore, 1188 $cm^2$), first with Buffer B to remove protein and then with Buffer C. The size of the beads was determined on the Nicomp and was approximately 316±55 nm (intensity weighted) in Buffer C. These beads were stored at 10 mg/mL in Buffer C.

Sensitizer beads having digoxin bound thereto were prepared as follows: Sens-beads having digoxin bound thereto were prepared (2 mg of beads at a final concentration of 0.5 mg/mL in Buffer C) as follows: The bis(biotin) digoxin conjugate from Example 7 was made 1 mM in DMF. The beads were light sensitive, so all operations were performed without overhead lighting (less than 5 lux). The 1 mM bis(biotin) digoxin conjugate was diluted 100-fold by diluting 5 μL to 0.5 mL of Buffer C to give a final concentration of 10 μM. The solution was diluted further to 125-fold by adding 16 μL of the 10 μM solution to 1984 μL of Buffer C to give a final concentration of 80 nM. The SAV-Sens-beads from above were diluted from 10 mg/mL to 1 mg/mL by diluting 200 μL of bead solution to 2000 μL with Buffer C.

The bead solution (2 mL at 1 mg/mL) was added to a 10 mL vessel along with a micro stir bar. To the stirred beads was added the 80 nM solution of bis(biotin) digoxin conjugate in 50 μL portions (40 total additions) over 15 min. Stirring was continued for 10 min following the last addition above and the beads were stored at 4° C.

Chemiluminescer beads having anti-digoxin antibody bound thereto were prepared as follows:

C-28 thioxene was prepared as follows:

To a solution of 4-bromoaniline (30 g, 174 mmol) in dry DMF (200 mL) was added 1-bromotetradecane (89.3 mL, 366 mmol) and N,N-diisopropylethylamine (62.2 mL, 357 mmol). The reaction solution was heated at 90° C. for 16 hr under argon before being cooled to room temperature. To this reaction solution was again added 1-bromotetradecane (45 mL, 184 mmol) and N,N-diisopropylethylamine (31 mL, 178 mmol) and the reaction mixture was heated at 90° C. for another 15 hr. After cooling, the reaction solution was concentrated in vacuo and the residue was diluted with $CH_2Cl_2$ (400 mL). The $CH_2Cl_2$ solution was washed with 1N aqueous NaOH (2×), $H_2O$, and brine, was dried over $Na_2SO_4$ and was concentrated in vacuo to yield a dark brown oil (about 110 g). Preparative column chromatography on silica gel by a Waters 500 Prep LC system eluting with hexane afforded a yellow oil that contained mainly the product (4-bromo-N,N-di-($C_{14}H_{29}$)-aniline) along with a minor component 1-bromotetradecane. The latter compound was removed from the mixture by vacuum distillation (bp 105–110° C., 0.6 mm) to leave 50.2 g (51%) of the product as a brown oil. To a mixture of magnesium turnings (9.60 g, 395 mmol) in dry THF (30 mL) under argon was added dropwise a solution of the above substituted aniline product (44.7 g, 79 mmol) in THF (250 mL). A few crystals of iodine were added to initiate the formation of the Grignard reagent. When the reaction mixture became warm and began to reflux, the addition rate was regulated to maintain a gentle reflux. After addition was complete, the mixture was heated at reflux for an additional hour. The cooled supernatant solution was transferred via cannula to an addition funnel and added dropwise (over 2.5 hr) to a solution of phenylglyoxal (11.7 g, 87 mmol) in THF (300 mL) at −30° C. under argon. The reaction mixture was gradually warmed to 0° C. over 1 hr an stirred for another 30 min. The resulting mixture was poured into a mixture of ice water (800 mL) and ethyl acetate (250 mL). The organic phase was separated and the aqueous phase was extracted with ethyl acetate (3×). The combined organic phases were washed with $H_2O$ (2×), brine and was dried over $MgSO_4$. Evaporation of the solvent gave 48.8 g of the crude product as a dark green oily liquid. Flash column chromatography of this liquid (gradient elution with hexane, 1.5:98.5, 3:97, 5:95 ethyl acetate:hexane) afforded 24.7 g (50%) of the benzoin product (MS ($C_{42}H_{69}NO_2$): [M-H]$^+$618.6, $^1$H NMR (250 MHz, $CDCl_3$) was consistent with the expected benzoin product. To a solution of the benzoin product from above (24.7 g, 40 mmol) in dry toluene (500 mL) was added sequentially 2-mercaptoethanol (25 g, 320 mmol) and TMSCI (100 mL, 788 mmol). The reaction solution was heated at reflux for 23 hr under argon before being cooled to room temperature. To this was added additional TMSCI (50 mL, 394 mmol) ;and the reaction solution was heated at reflux for another 3 hr. The resulting solution was cooled, was made basic with cold 2.5N aqueous NaOH and was extracted with $CH_2Cl_2$ (3×). The combined organic layers were washed with saturated aqueous $NaHCO_3$ (2×) and brine, was dried over $Na_2SO_4$ and was concentrated in vacuo to give a brown oily liquid. Preparative column chromatography on silica gel by using a Waters 500 Prep LC system (gradient elution with hexane, 1:99, 2:98 ethyl acetate:hexane) provided 15.5 g (60%) of the C-28 thioxene as an orange-yellow oil (MS ($C_{44}H_{71}NOS$): [M-H]$^+$661.6, $^1$H NMR (250 MHz, $CDCl_3$) was consistent with the expected C-28 thioxene product 2-(4-(N,N-di-($C_{14}H_{29}$)-anilino)-3-phenyl thioxene.

Carboxyl acceptor beads were prepared as follows:

The starting beads were carboxylate modified latex purchased from Seradyn Particle Technology, Indianapolis, Ind.

The beads contained Eu(TTA)$_3$DPP prepared as follows: DPP/Eu(TTA)$_3$ was prepared by combining 8.69 g of Eu(TTA)$_3$. 3H$_2$O (10 mmoles, Kodak Chemical Company, Rochester N.Y.) and 1.8 g of 1,10-phenanthroline (10 mmoles, Aldrich) in 50 ml of dry toluene and heating to 95° C. in an oil bath for one 1 hr. Toluene was removed under reduced pressure. The ash colored solid was crystallized from 100 ml of toluene to yield 10 grams of DPP/Eu(TTA)$_3$. Absorption spectrum: 270 nm (20,000), 340 nm (60,000) (Toluene) 1.R(KBr): Cm$^{-1}$: 3440(s), 1600(s), 1540(s), 1400 (s), 1300(s). Four mL of 20% suspension (400 mg) of washed 175 nm carboxylate modified latex was diluted with 3 mL of ethoxyethanol in a 25 mL round bottom (R.B.) flask with a stir bar. The R.B. flask was then placed in an oil bath at 105° C. and stirred for 10 min. Then, 3.3 mM C-28 thioxene and 15.5 mM Eu(TTA)$_3$DPP was added; the beads were stirred for 5 min more. At this point 1.0 mL of 0.1N NaOH was added slowly over 5 min. During all the additions, the oil bath temperature was maintained at 105° C. The oil bath temperature was slowly allowed to drop to room temperature over 2 hr. After cooling, the mixture was diluted with 20 mL of ethanol and centrifuged (12,500 rpm, 30 min). Supernatants were discarded and the pellets resuspended in ethanol by sonication. Centrifugation was repeated, and the pellet was resuspended in water; and centrifugation was repeated. The pellet was resuspended in 5 mL of aqueous ethanol to a final volume of 40 mL.

The above beads were treated to bind monoclonal anti-digoxin antibody thereto in a manner similar to that described above for the binding of streptavidin to the Sens-beads. Monoclonal anti-digoxin antibody (prepared as described above) was purified by ABx resin (Baker Chemical Company, Phillipsburg, N.J.) and was dialyzed into 0.15 M NaCl, 5 mM Na$_2$HPO$_4$, pH 7.4 (17.8 mg/mL). The bead size, determined using the Nicomp particle size analyzer, was 330–380 nm±100 nm. The number of antibody molecules per bead was approximately 20.

An assay for digoxin was conducted as follows:

A set of human serum calibrators containing 0, 0.5, 1.5, 3.0 and 5.0 ng/mL was prepared. A sample (20 μL) was combined with 0.5 mg/mL anti-digoxin coated chemiluminescer beads (prepared as described above) and 360 μL Buffer C. The reaction mixture was incubated for 108.5 sec and 20 μL of 0.1 mg/mL digoxin coated Sens-beads (prepared as described above) plus 580 μL of Buffer C was added. The reaction mixture was incubated for 170 sec. The reaction mixture was then irradiated with a 150 watt Xenon lamp for 3 sec (3 cycles of 1 sec illumination and 1 sec waiting time) and the signal was then read.

The results of a typical experiment conducted according to this Example 8 were as follows (Table 1):

TABLE 1

| Digoxin (ng/mL) | Signal (RLU) |
|---|---|
| 0 | 100 |
| 0.5 | 82 |
| 1.5 | 55 |
| 3.0 | 33 |
| 5.0 | 22 |

EXAMPLE 9

Assay for Thyroxine

Materials and Methods:

All reagents were reagent grade and were used without further purification. Light was excluded from photo-sensitive compounds by wrapping flasks in foil or black fabric under subdued lab lighting. "Chromatotron" is a rotary preparative chromatography system available from Harrison Research, Palo Alto, Calif. Silica gel 250 analytical plates were obtained from Analtech. $^1$H-NMR was recorded on a Bruker 250 MHz FT-NMR Spectrometer using deuterated solvents obtained from Aldrich. Particle sizing was done on a NICOMP Model 370. Assays were run on the TECAN 3 (from Tecan U.S. SLT Lab instruments). T4Bi$_2$= thyroxine conjugated to bisbiotin of the invention.

Synthesis of reagents:

I. T4Bi$_2$-SAv-Sensitizer Beads:

A. Preparation of N-Acetylthyroxine-N'-hydroxysuccinimide ester T4-NHS.

N-Acetylthyroxine was prepared in a manner similar to that described by Adamczyk, M., *Bioconjugate Chem.* (19.94) 5(5):459–462. The N-Acetylthyroxine (37.3 mg, 0.0455 mmol), N-hydroxysuccinimide (5.8 mg, 0.050 mmol), and EDAC (10.6 mg, 0.055 mmol) were dissolved in 0.2 mL degassed DMF. The thyroxine was completely consumed after stirring for 4 hr at ambient temperature. The crude reaction mixture was used directly in the next step. (tlc: SiO$_2$: (1:4) H$_2$O-ACN as the dimethylamine derivative).

B. Deprotection of t-BOC-bisbiotin.

The t-BOC-bisbiotin (prepared as described above) (37.8 mg, 0.0356 mmol) was suspended in 0.5 mL dichloromethane. Addition of 50 uL trifluoroacetic acid (TFA) gave a clear solution. A second addition of 25 uL TFA was necessary to drive the reaction to completion in 2 hr at ambient temperature. Volatiles were removed by rotary evaporation. After the residue was twice concentrated to dryness from 3 mL portions of dichloromethane, it was further dried for 1 hr at ambient temperature under 0.1 mm Hg vacuum. (tlc: SiO$_2$: (1:4) H$_2$O-ACN, 5 uL dried with argon, treatment with TEA/methanol (MeOH)/CH$_2$CH$_2$.

C. Preparation of N-Acetylthyroxine-bisbiotin hapten.

The bisbiotin from above (0.36 mmol) and the crude solution of T4-NHS from above (200 uL, ca. 0.046 mmol) were combined in dichloromethane (0.10 mL) and triethylamine (0.040 mL, 0.3 mmol). The pH of the mixture was about 7 (wetted paper). The reaction was judged to be complete (tlc) after stirring at ambient temperature for 3 hr. The product was partially purified by precipitation with ether from MeOH-CH$_2$Cl$_2$. A portion (½) of the partially purified product was applied as a MeOH-CH$_2$Cl$_2$ solution to a pre-equilibrated (10% H$_2$O/ACN) 1 mm silica gel Chromatotron rotor. The T4Bi$_2$ was collected as a single band by gradient elution (10–15% H$_2$O/ACN). The product was precipitated by removal of ACN by rotary evaporation. Centrifugation (30 min, 2500 rpm) gave a white pellet which was washed with ether and dried overnight at ambient temperature under 0.1 mm Hg vacuum affording 5 mg of pure T4Bi$_2$. (tlc: SiO$_2$: (1:4) H$_2$O-ACN, UV254, biotin spray reagent); ms: M79584: MW 1734, (M+H)$^+$1734.8; nmr: all peaks corresponded to expected product.

D. Preparation of T4Bi$_2$-SAv-Sensitizer Beads.

A portion (0.8498 mg, 4.90×10$^{-4}$ mmol) of the T4Bi$_2$ from above was dissolved in 1.00 mL DMF. A 15 μL aliquot of the solution was successively diluted with Buffer C to give a range of seven concentrations from 0.15×10$^{-6}$ to 2.45×10$^{-6}$ mmol / mL (designed to give the loadings described in Part III). These solutions (0.9 mL each) were transferred under the surface of vortexing 1.00 mg / mL suspensions of SAV-Sens-beads prepared as described above in Example 8 contained in seven corresponding 10 cc tubes. The tubes were incubated for 1 hr at ambient temperature.

The beads were sized using the NICOMP Submicron Particle Sizer (all beads were within 306–317 nm±18–29%).

II. MAbT$_4$ Acceptor Beads

Monoclonal anti-T4 antibodies were prepared as described above and were bound to Acc-beads as described above in Example 8 for binding of monoclonal anti-digoxin antibodies to Acc-beads.

III. Assay for thyroxine (T4):

Using the TECAN 3 instrument, 20 uL samples of the 0.5 mg / mL MAbT4 Acc-beads were incubated in turn with each of a set of five free thyroxine (FT4) calibrators (0, 0.8, 2.2, 3.5, and 6.7 ng / dL). After each incubation, a 20 uL sample of the 0.5 mg / mL T4Bi$_2$-SAv-Sens-bead reagents was added followed by a second incubation period. The results are summarized in Table 2.

TABLE 2

| FT4 (ng/dL) | Signal (RLU) |
| --- | --- |
| 0 | 220,000 |
| 0.8 | 192,000 |
| 2.2 | 150,000 |
| 3.5 | 120,000 |
| 6.7 | 75,000 |

EXAMPLE 10

Assay for Estradiol

Bisbiotinylated estradiol was prepared in a manner similar to that described above in Example 7 for preparation of bisbiotinylated digoxin. Binding of bisbiotinylated haptens to streptavidin particles was carried out in assay buffer (Buffer C). A dilute solution of the bisbiotinylated hapten (30–2000 nM) was added dropwise to an equivolume solution containing 1 mg/mL streptavidin beads and the reaction incubated at 25° C. for 1 hr. Binding was quantitative. Dynamic light scattering measurements showed that no significant bead aggregation had occurred.

The assay diluent contained 20 ng/mL 5α-dihydrotestosterone as a releasing agent to displace estradiol for serum steroid binding proteins. The serum sample (50 μL) was combined with 350 μL of reagent 1 containing 10 μg chemiluminescer particles coated with an IgG fraction of a rabbit anti-estradiol antiserum (Cat. No. D1065JR, lot 084, Biodesign International, Kennebunk, Me.). Following incubation at 37° C. for 10 min, 600 μL of reagent 2 containing 10 μg streptavidin coated sensitizer particles labeled with 700 molecules of bisbiotinylated estradiol per particle was added and the incubation continued for 10 min. The chemiluminescent signal was measured by irradiating with ten-one sec pulses at 680 nm and integration of the light emitted at 580 to 620 nm for one sec following each pulse.

Signal modulation at 150 and 500 μg/mL estradiol was 23 and 43%, respectively. Upon assaying 37 patient sera for estradiol by this method and by the DPC Coat-A-Count RIA method (Diagnostic Products Company, Los Angeles, Calif.), a correlation (R) of 0.990 was obtained.

EXAMPLE 11

Assay for Cyclosporin

Bisbiotinylated cyclosporin was prepared in a manner similar to that described above in Example 7 for preparation of bisbiotinylated digoxin. Binding of bisbiotinylated haptens to streptavidin particles was carried out in assay buffer (Buffer C). A dilute solution of the bisbiotinylated hapten (30–2000 nM) was added dropwise to an equivolume solution containing 1 mg/mL streptavidin beads and the reaction incubated at 25° C. for 1 hr. Binding was quantitative. Dynamic light scattering measurements showed that no significant bead aggregation had occurred.

Whole blood (0.05 mL) was diluted with 0.08 mL of 5% sodium dodecyl sulfate (SDS) and 1.25 mL of 8% propylene glycol. A 20 μL aliquot of the pretreated sample was combined simultaneously with 150 ng anti-hydroxylcyclosporin antibody to scavenge the M-1 metabolite of cyclosporin and 5 μg chemiluminescer particles coated with anti-cyclosporin antibody in a volume of 400 μL. Following incubation at 37° C. for 4.5 min, 400 μL of a solution containing 5 μg streptavidin coated sensitizer particles labeled with 1850 molecules of bisbiotinylated cyclosporin per particle was added and the incubation continued for 4.5 min. The chemiluminescent signal was measured as in the digoxin assay. The chemiluminescent signal was measured by irradiating with ten-one sec pulses at 680 nm and integration of the light emitted at 580 to 620 nm for one sec following each pulse.

A standard curve was constructed using the above assay procedure and calibrators in whole blood. There was signal modulation of 21% with the low (50 ng/mL) calibrator and 74% with the high (500 ng/mL) calibrator. The susceptibility of this assay to the whole blood matrix was evaluated by assaying 40 negative samples resulting in a signal CV of 1.6%. The precision of this assay was estimated by assaying three patient samples in 20 replicates. CV's of 8.1%, 2.7% and 2.5% were observed for 53.6, 249.7 and 473.9 ng/mL samples, respectively. Correlation with a standard procedure was determined using 50 fresh patient samples in which cyclosporin had been determined using high performance liquid chromatography (HPLC). The resultant correlation was R=0.95, R$^2$=0.91 and a slope of 0.88.

EXAMPLE 12

Stability Studies for Complex of Bis-biotin-digoxigenin Conjugate and Streptavidin Coated Sensitizer Beads A. A solution of the bis-biotin-digoxigenin conjugate of Example 7 was prepared containing 3.0×10$^{-7}$ M of the conjugate in Buffer C. As a control a solution of a mono-biotin-digoxigenin conjugate (the same molecule as the bis-biotin conjugate but with one biotin per conjugate molecule rather than two) was prepared containing 3.0×10$^{-7}$ M of the conjugate in Buffer C. The mono-biotin-digoxigenin conjugate was prepared in a manner similar to that described above for the preparation of the bis-biotin-digoxigenin conjugate with 3-nitrobenzoylchloride in place of 3,5-dinitrobenzoylchloride.

An 37 mL aliquot of the bis-biotin-digoxigenin solution from above was added dropwise at 10° C. to a vortexing 37 mL solution of the sensitizer-streptavidin coated sensitizer beads prepared as described above in Example 8 (1 mg beads/mL). An 18.7 mL aliquot of the mono-biotin-digoxigenin solution from above was added dropwise at 10° C. to a vortexing 18.75 mL solution of the streptavidin coated sensitizer beads from above (1 mg beads/mL). After overnight storage of each of the above solutions at 4° C., the beads were diluted with an equivalent volume of either 2.5×10$^{-5}$ M biotin in Buffer C or Buffer C itself. These solutions were then incubated using constant temperature water baths at 37° C. in the absence of light. At intervals, a 0.5 mL aliquot was withdrawn, cooled in an ice water bath, and centrifuged in 1.5 mL Eppendorf tubes for 25 min, 15K, 4° C., 400 µL of supernatant were withdrawn and stored at 4° C. for later evaluation in a digoxin assay. The results of the stability studies are summarized in Table 3.

TABLE 3

| Hours | Bis-biotin-digoxigenin (nM) | Mono-biotin-digoxigenin (nM) |
|---|---|---|
| 0 | 0 | 0 |
| 4.5 | 0 | 9.3 |
| 21 | 0 | 18.6 |
| 74 | 0 | 23.1 |
| 143 | 0 | 33.8 |
| 166 | 0 | 34.9 |
| 190 | 0 | 35.7 |
| 214 | 0 | 37.0 |
| 262 | 0 | 37.5 |
| 382 | 0 | 41.2 |
| 490 | 0 | 43.5 |

As can be seen from the above data, the bis-biotin-digoxigenin conjugate in accordance with the present invention exhibited no dissociation from its complex with streptavidin when incubated in the presence of $1 \times 10^{-5}$ biotin at 37° C. for 490 hr whereas the mono-biotin-digoxigenin conjugate (control, not part of the present invention) exhibited approximately 43% dissociation from its complex with streptavidin when incubated under the above conditions.

B. Another stability study was carried out using the above bis-biotin-digoxigenin conjugate and sensitizer-streptavidin beads in a buffer containing 50 mM KCl, 0.2 mg BSA/mL, 10 mM TRIS, pH 8.3, in the presence of $10^{-4}$ M biotin at 95° C. Less than 1% dissociation of the complex of bis-biotin-digoxigenin conjugate with sensitizer-streptavidin beads to give free bis-biotin-digoxigenin conjugate was observed.

The above discussion includes certain theories as to mechanisms involved in the present invention. These theories should not be construed to limit the present invention in any way, since it has been demonstrated that the present invention achieves the results described.

The above description and examples fully disclose the invention including preferred embodiments thereof. Modifications of the methods described that are obvious to those of ordinary skill in the art such as molecular biology and related sciences are intended to be within the scope of the following claims.

What is claimed is:

1. A compound that is a bis-biotin comprising two biotinyl radicals connected by a chain at least 16 atoms in length having a 1,3-disubstituted aromatic ring as part of said chain, said chain being conjugated to a member of a specific binding pair ("sbp member") wherein said chain is not part of said sbp member, and wherein said biotinyl radicals substantially exclusively bivalently bind with a single molecule of avidin.

2. The compound of claim 1 wherein said member of a specific binding pair is conjugated to said chain by an attaching group.

3. The compound of claim 2 wherein said attaching group comprises a linking member to said sbp member selected from the group consisting of ether, thioether, carbonyl, iminocarbonyl, amine, sulfonamide and phosphate ester.

4. The compound of claim 1 wherein said chain is from 16 to 30 atoms in length.

5. The compound of claim 1 wherein said chain is from 17 to 21 atoms in length.

6. The compound of claim 1 wherein said sbp member is selected from the group consisting of haptens, antigens, receptors and polynucleotides.

7. A composition comprising a complex of avidin and a molecule having two biotinyl radicals connected to one another by a chain at least 16 atoms in length, said chain being conjugated to a member of a specific binding pair ("sbp member") wherein said chain is not part of said sbp member, said chain having a 1,3-disubstituted aromatic ring as part of said chain and said biotinyl radicals are substantially exclusively bivalently bound to said single molecule of avidin.

8. The composition of claim 7 wherein said avidin is streptavidin.

9. The composition of claim 7 wherein said avidin is bound to a support.

10. The composition of claim 7 wherein said member of a specific binding pair is conjugated to said chain by an attaching group.

11. The composition of claim 10 wherein said attaching group comprises a linking member to said sbp member selected from the group consisting of ether, thioether, carbonyl, iminocarbonyl, amine, sulfonamide and phosphate ester.

12. The composition of claim 7 wherein said chain is from 16 to 30 atoms in length.

13. The composition of claim 7 wherein said chain is from 17 to 21 atoms in length.

14. The composition of claim 7 wherein said sbp member is selected from the group consisting of haptens, antigens, receptors and polynucleotides.

15. The composition of claim 7 wherein said chain contains at least 5 atoms in a rigid spatial array.

16. The composition of claim 7 wherein said chain contains at least two sets of at least 4 atoms in a rigid spatial array.

17. In an assay for an analyte wherein there is employed a reagent system comprising an avidin reagent and a biotin reagent, the improvement comprising using as the biotin reagent a composition comprising two biotinyl radicals connected by a chain at least 16 atoms in length having a 1,3-disubstituted aromatic ring as part of said chain, wherein said biotinyl radicals substantially exclusively bivalently bind to a single molecule of avidin, wherein a member of a specific binding pair ("sbp member") is conjugated to said chain, and wherein none of the atoms of said chain is part of said sbp member.

18. The assay of claim 17 wherein said avidin is streptavidin.

19. The assay of claim 17 wherein said avidin is bound to a support.

20. The assay of claim 17 wherein said sbp member is conjugated to said chain by a linking member selected from the group consisting of ether, thioether, carbonyl, iminocarbonyl, amine, sulfonamide and phosphate ester.

21. The assay of claim 17 wherein said chain is from 16 to 30 atoms in length.

22. The assay of claim 17 wherein said chain is from 17 to 21 atoms in length.

23. The assay of claim 17 wherein said sbp member is selected from the group consisting of haptens, antigens, receptors and polynucleotides.

24. The assay of claim 17 wherein said chain contains at least two sets of at least 4 atoms in a rigid spatial array.

25. A kit comprising in packaged combination:

(a) an avidin reagent for use in a specific binding assay and (b) a compound consisting of a bis-biotin comprised of two biotinyl radicals connected by a chain at least 16 atoms in length, said bis-biotin being conjugated to a member of a specific binding pair ("sbp member") wherein said chain is not part of said sbp member and said chain has a 1,3-disubstituted aromatic ring as part of said chain such that said biotinyl radicals substantially exclusively bivalently bind to a single molecule of avidin.

26. The kit of claim 25 wherein said avidin reagent comprises streptavidin.

27. The kit of claim 25 wherein said avidin reagent comprises avidin bound to a support.

28. The kit of claim 25 wherein said sbp member is selected from the group consisting of haptens, antigens, receptors and polynucleotides.

29. The kit of claim 25 wherein said sbp member is conjugated to said chain by a linking member selected from the group consisting of ether, thioether, carbonyl, iminocarbonyl, amine, sulfonamide and phosphate ester.

30. The kit of claim 25 wherein said chain is from 16 to 30 atoms in length.

31. The kit of claim 25 wherein said chain is from 17 to 21 atoms in length.

32. The kit of claim 25 wherein said chain contains at least two sets of at least 4 atoms in a rigid spatial array.

33. A method of preparing a bis-biotinylated conjugate of a member of a specific binding pair ("sbp member") for use in a specific binding assay comprising the step of reacting said sbp member with a molecule containing two biotinyl radicals connected by a chain of at least 16 atoms having a 1,3-disubstituted aromatic ring as part of said chain, said chain comprising an attaching group for attaching said molecule to said sbp member, and wherein said biotinyl radicals substantially exclusively bivalently bind with a single molecule of avidin.

34. A complex of (i) a compound that is bis-biotin comprising two biotinyl radicals connected together by a chain of at least 16 atoms including a 1,3-disubstituted aromatic ring as part of said chain, said bis-biotin being conjugated to a member of a specific binding pair ("sbp member") wherein said chain is not part of said sbp member and (ii) avidin, wherein said biotinyl radicals are substantially exclusively bivalently bound to a single molecule of avidin and wherein said complex remains substantially intact when stored for two weeks at 37° in a $10^{-6}$ M biotin solution.

35. A composition comprising avidin complexed with a bis-biotin having a chain, connecting the two biotinyl radicals, of at least 16 atoms including a 1,3-disubstituted aromatic ring as part of said chain wherein said complexes have only one or two bis-biotin molecules substantially exclusively bivalently bound to each avidin molecule.

36. A compound comprising two biotinyl radicals covalently bound together by a linking group comprising a chain of atoms at least 16 atoms in length including a 1,3-disubstituted aromatic ring as part of said chain wherein said biotinyl radicals substantially exclusively bivalently bind with a single molecule of avidin, said chain having an attaching group bound thereto, wherein, when a solution containing (i) less than or equal to $10^{-8}$ M of a 1:1 mole:mole complex of said compound and fully active avidin and (ii) $10^{-6}$ M free biotin is incubated at 37° C. for at least 14 days, said complex exhibits less than 1% dissociation.

37. The compound of claim 36 wherein a member of a specific binding pair is conjugated to said attaching group.

38. The compound of claim 36 wherein a group detectable by means of electromagnetic radiation or electrochemical detection is conjugated to said attaching group.

39. The compound of claim 36 wherein said chain of atoms is from 16 to 30 atoms in length.

40. The compound of claim 36 wherein said attaching group contains a functionality selected from the group consisting of thiol, carboxy, hydroxy, thiocyanate, primary amine, secondary amine and haloacetamide.

41. A compound that is a bis-biotin comprising two biotinyl radicals connected by a chain at least 16 atoms in length including a 1,3-disubstituted aromatic ring as part of said chain wherein said biotinyl radicals substantially exclusively bivalently bind with a single molecule of avidin, said chain comprising a functionality reactive with a corresponding functionality of a protein, said functionality and said corresponding functionality further characterized in that their reaction with each other does not substantially affect the activity of said protein.

42. The compound of claim 41 wherein said functionality is a non-oxocarbonyl.

43. The compound of claim 41 wherein said corresponding functionality is amino or sulfhydryl.

* * * * *